(12) United States Patent
Cohen et al.

(10) Patent No.: US 6,541,459 B1
(45) Date of Patent: *Apr. 1, 2003

(54) SOLUBLE HERPESVIRUS GLYCOPROTEIN COMPLEX VACCINE

(75) Inventors: Gary H. Cohen, Havertown, PA (US); Roselyn J. Eisenberg, Haddonfield, NJ (US); Tao Peng, San Diego, CA (US); Gary Dubin, La Hulpe (BE)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/658,056

(22) Filed: Sep. 8, 2000

Related U.S. Application Data

(60) Division of application No. 08/904,484, filed on Jul. 31, 1997, now Pat. No. 6,156,319, which is a continuation-in-part of application No. 08/280,442, filed on Jul. 25, 1994, now Pat. No. 5,807,557.

(51) Int. Cl.$^7$ ............................................... A01N 43/04
(52) U.S. Cl. ................... 514/44; 424/186.1; 424/193.1; 424/231.1; 435/69.3; 435/325; 435/354; 435/455
(58) Field of Search .................. 514/44; 424/184.1, 424/186.1, 193.1, 231.1; 435/325, 69.3, 354, 455

(56) References Cited

U.S. PATENT DOCUMENTS

| | | | |
|---|---|---|---|
| 4,053,585 A | 10/1977 | Allison et al. | |
| 4,082,735 A | 4/1978 | Jones et al. | |
| 4,082,736 A | 4/1978 | Jones et al. | |
| 4,101,536 A | 7/1978 | Yamamura et al. | |
| 4,185,089 A | 1/1980 | Derrien et al. | |
| 4,235,771 A | 11/1980 | Adam et al. | |
| 4,261,975 A | 4/1981 | Fullerton et al. | |
| 4,291,019 A | 9/1981 | Lupton et al. | |
| 4,406,890 A | 9/1983 | Tarrsay et al. | |
| 4,606,918 A | 8/1986 | Allison et al. | |
| 4,661,349 A | 4/1987 | Kino et al. | |
| 4,689,225 A | 8/1987 | Pereira | |
| 5,149,529 A | 9/1992 | Ho et al. | |
| 5,224,792 A | 7/1993 | Burke et al. | |
| 5,474,914 A | 12/1995 | Spaete | |
| 5,807,557 A | * 9/1998 | Dubin ..................... | 424/231.1 |
| 6,156,319 A | * 12/2000 | Cohen et al. .......... | 424/196.11 |

FOREIGN PATENT DOCUMENTS

| | | |
|---|---|---|
| WO | WO 89/07615 | 8/1989 |
| WO | WO 89/10965 | 11/1989 |
| WO | WO 90/11302 | 10/1990 |
| WO | WO 91/02004 | 2/1991 |
| WO | WO 92/01057 | 1/1992 |
| WO | WO 92/05263 | 4/1992 |
| WO | WO94/21807 | 9/1994 |

OTHER PUBLICATIONS

Bourne et al. Vaccine 14(13): 1230–1234, 1996.*
McClements et al. Proceedings of the National Academy of Sciences USA 93:11414–11420., 1996.*
Mester, et al., 1991, Reviews of Infectious Diseases, 13:5935–5945.
Andersson et al., 1989. J. of Biological Chemistry, 264:8222–8229.
Blochlinger et al., 1984, Molecular and Cellular Biology, 4:2929–2931.
Cines et al., 1982, J. Clin. Invest., 69:123–128.
Cohen et al., 1986, J. of Virol., 60:157–166.
Cranage et al., 1988, J. of Virol., 62:1416–1422.
Davison et al., 1986,J. Gen. Virol., 67:1759–1816.
Desai et al., 1988, J. Gen. Virol., 69:1147–1156.
Farrell et al., 1994, J. Virol., 68:928.
Foa–Tomasi et al., 1991, Virol., 180:474–482.
Forrester et al., 1992, J. of Virol., 66:341–348.
Friedman et al., 1989, Molecular andCellular Biology, 9:2303–2314.
Fuller et al., 1989, J. of Virol., 63:3435–3443.
Gompels et al., 1986, Virol., 153:230–247.
Gompels et al., 1988, J. Virol., 69:2819–2829.
Gompels et al., 1989, J. of Virol., 63:4744–4755.
Graham et al., 1973, Virol., 52:456–467.
Josephs et al., 1991, J. of Virol., 65:5597–5604.
Kaye et al., 1992, J. of Gen. Virol., 73:2693–2698.
Klupp et al., 1991, Virol., 182:732–741.
McGeoch et al., 1986, Nucleic Acids Research, 14:4281–4292.
McGeoch et al., 1988, J. Gen. Virol., 69:1531–1574.
Peeters et al., 1992, J. Virol., 66:3888–3892.
Shawalter et al., 1981, Infection of Immunity, 34:684–692.
White, 1992, Science, 258:917–924.
Ghiasi et al., 1994., J. Virol., 68–4:2118–2126.
Roop et al., 1993, J. Virol., 67–4:2285–2297.
Ghiasi et al., 1992, J. Gen. Virol., 73:719–722.
Gompels et al., 1991, J. Virol., 65:2393–2401.
Ghiasi et al., 1991, Virol., 185:187–194.
Roberts et al., 1991, Virology, 184:609–624.
Buckmaster et al., 1984, Virology, 139:408–413.
Fuller et al., 1989, J. Virol., 63–8:3435–3443.
Browne et al., 1993, J. Gen. Virol. 74:2813–2817.
Spaete et al., 1993, Virol., 193:853–861.

(List continued on next page.)

*Primary Examiner*—Mary E. Mosher
(74) *Attorney, Agent, or Firm*—Morgan, Lewis & Bockius, LLP

(57) ABSTRACT

The invention is directed to a herpes simplex virus vaccine comprising a herpes simplex virus glycoprotein H-glycoprotein L complex. The invention is also directed to a vaccine comprising a DNA encoding a herpes simplex virus glycoprotein H-glycoprotein L complex. Also included is an antibody which specifically binds to a herpes simplex virus glycoprotein H-glycoprotein L complex and DNA encoding the same.

9 Claims, 16 Drawing Sheets

OTHER PUBLICATIONS

Yaswen et al., 1993, Virol., 195:387–396.
Hutchinson et al., 1992, J. Virol., 66:2240–2250.
Liu et al., 1993, J. Gen. Virol., 74:1847–1857.
Liu et al., 1993, Virol. 197:12–22.
Burton et al., 1994, *Adv. Immunol.* 57:191–280.
Davis–Poynter et al, 1994, J. Virol. 68:7586–7590.
Dubin et al. 1995, J. Virol. 69:4564–4568.
Eisenberg et al., 1987, Microb. Pathog. 3:423–435.
Eisenberg et al., 1982, J. Virol. 41:1099–1104.
Forrester et al., 1991, J. Gen. Virol. 72:369–375.
Friedman et al., 1989, Mol. Cell. Biol. 9:2303–2314.
Goldstein et al., 1988, J. Virol. 62:2970–2977.
Highlander et al., 1987, J. Virol. 61:3356–3364.
Johnson et al., 1990, J. Virol. 64:2569–2576.
Ligas et al., 1988, J. Virol 62–1486.
Montgomery et al., 1996, Cell. 87:427–436.
Nicola et al., 1997, J. Virol. 71:2940–2946.
Nicola et al., 1996. J. Virol. 70:3815–3822.
Novotny et al., 1996, Virology 221:1–13.
Sambrook et al., 1989, Molecular Clonining: A Laboratory Manual, Colg Spring Harbor, NY, pp. 16.14, 16.30 and 16.31.
Simmons et al., 1985, J. Virol. 53:944–948.
Simmons et al., 1984, J. virol. 52:816–821.
Sisk et al., 1994, J. Virol. 68:766–775.
Stanberry, Pathogenesis of herpes simplex virus infection and animal models for its study. In: Current Topics in Microbiology and Immunology, 179: Herpes simplex virus: Pathogenesis and Control, Springer Verlag (Berlin), 1992, pp. 15–30.
Tal–Singer et al., 1995, J. Virol. 69:4471–4483.
Wang et al., 1993, Proc. Natl. Acad. Sci. USA 90:4156–4160.
Whitbeck et al., 1997, J. Virol. 71:6083–6093.
Wright et al., 1992, Critical Rev. in Immunol. 12(3,4):125–168.
Chan et al., 1985, J. Exp. Med., 162:1304–1318.
Long et al., 1984, Infection and lmmunity, 37:761–764.

* cited by examiner

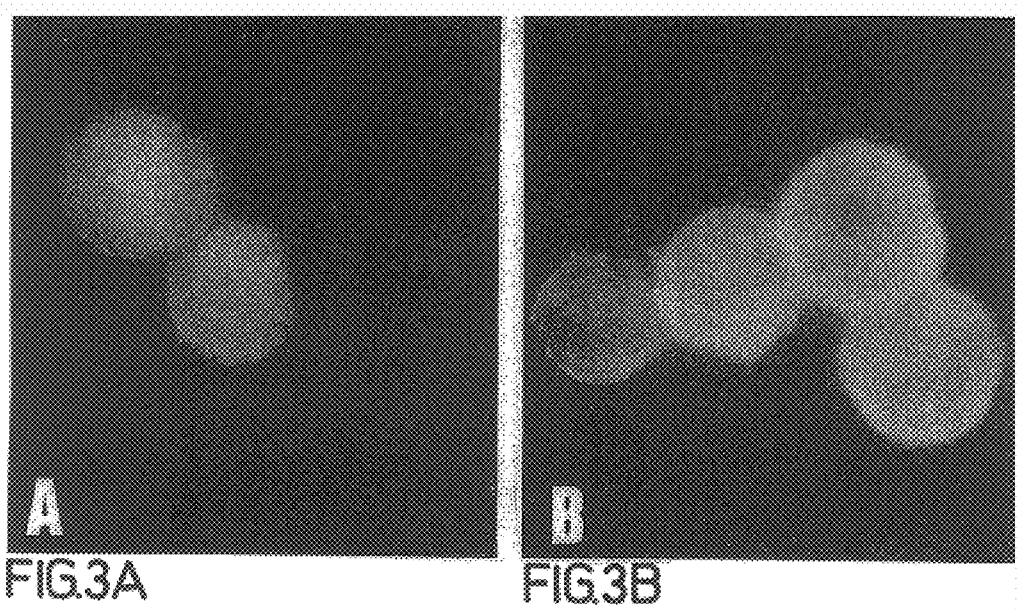
FIG.3A  FIG.3B
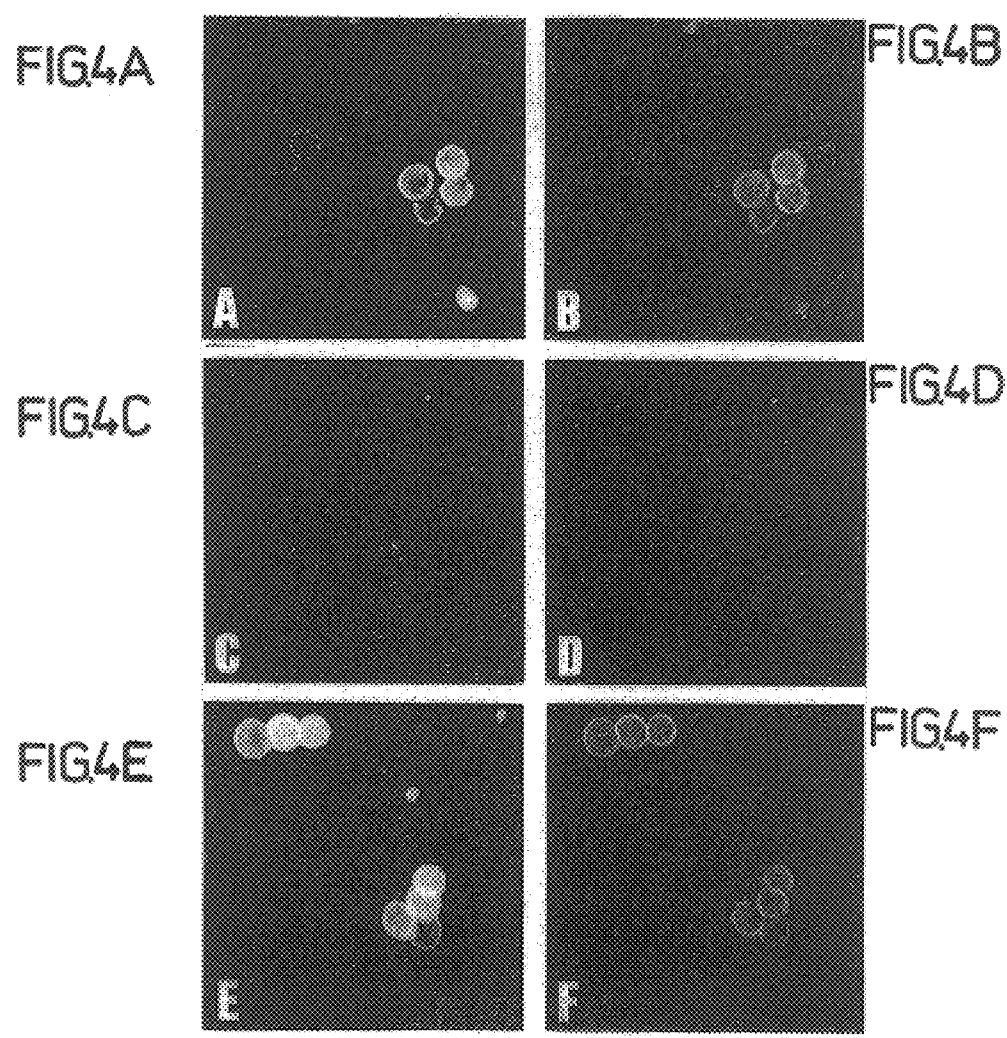
FIG.4A  FIG.4B
FIG.4C  FIG.4D
FIG.4E  FIG.4F

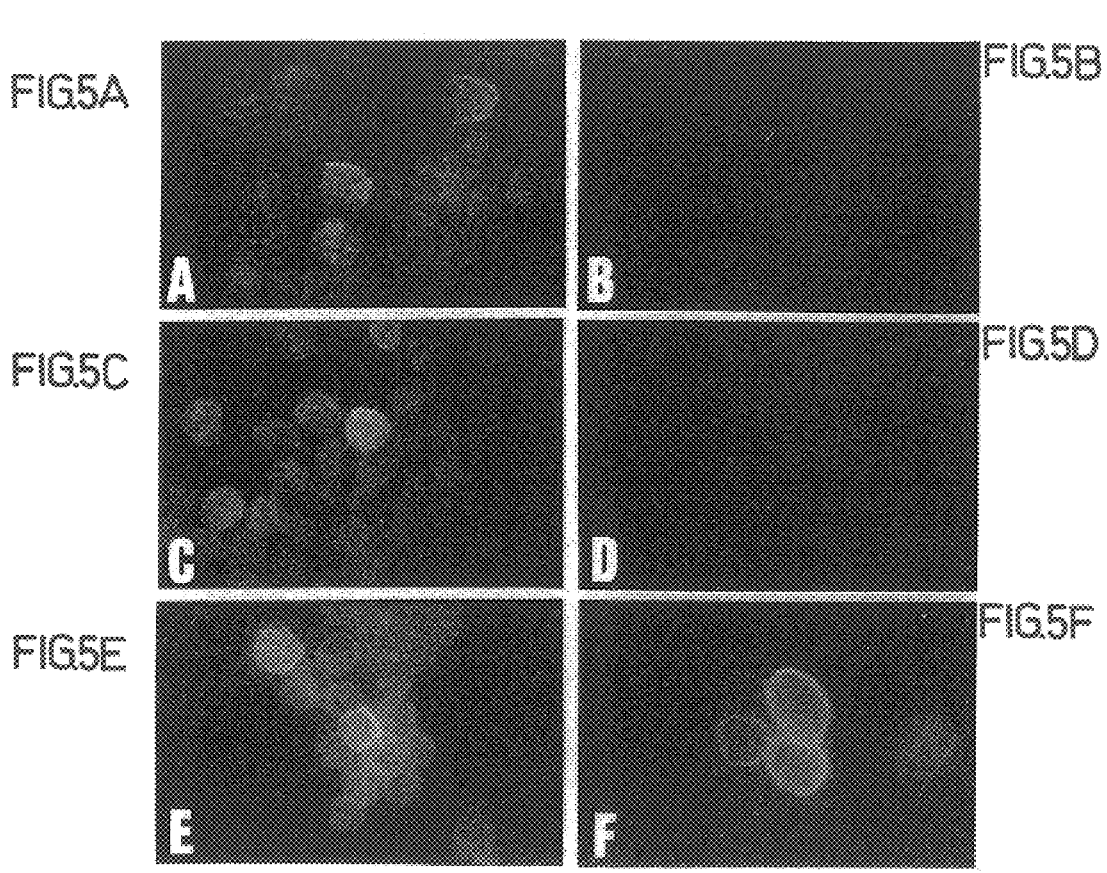

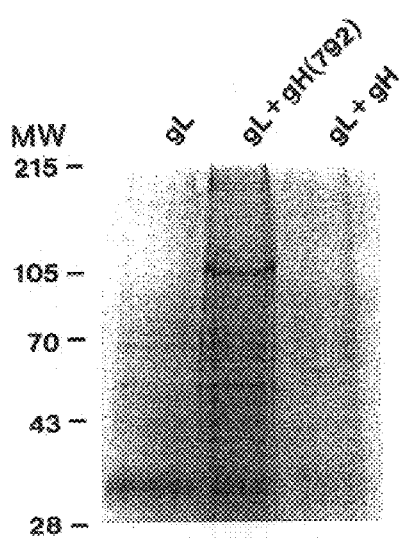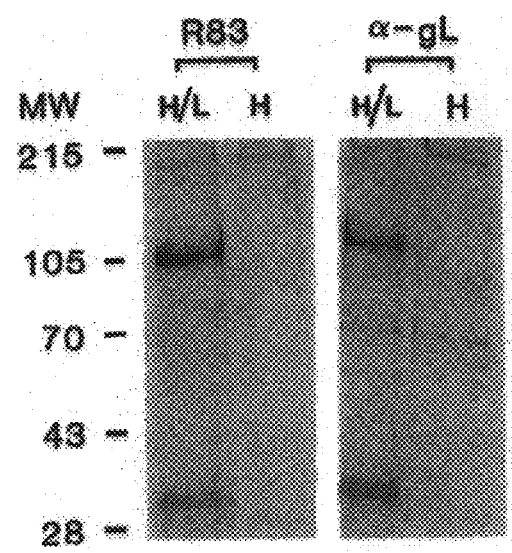
FIG.6
FIG.7

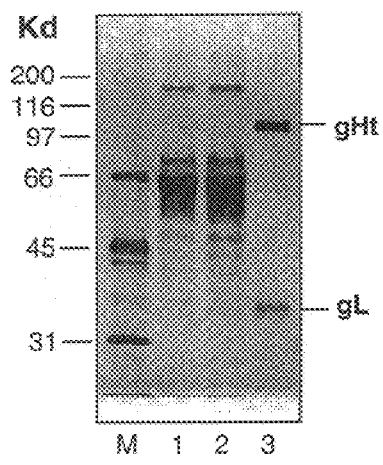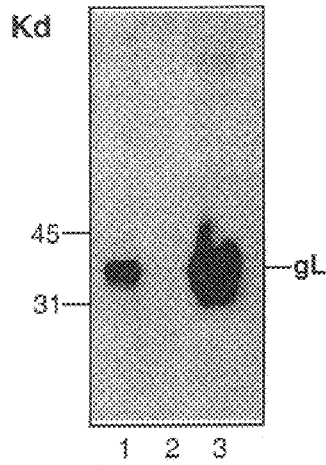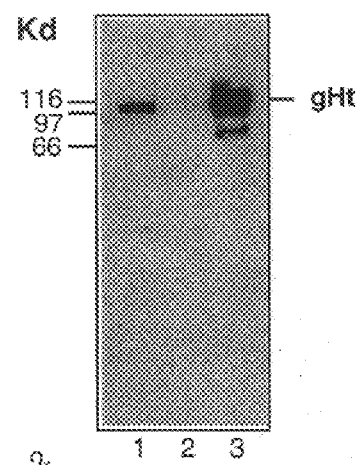
FIG.13A  FIG.13B  FIG.13C
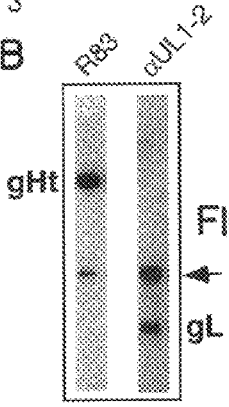
FIG.14A

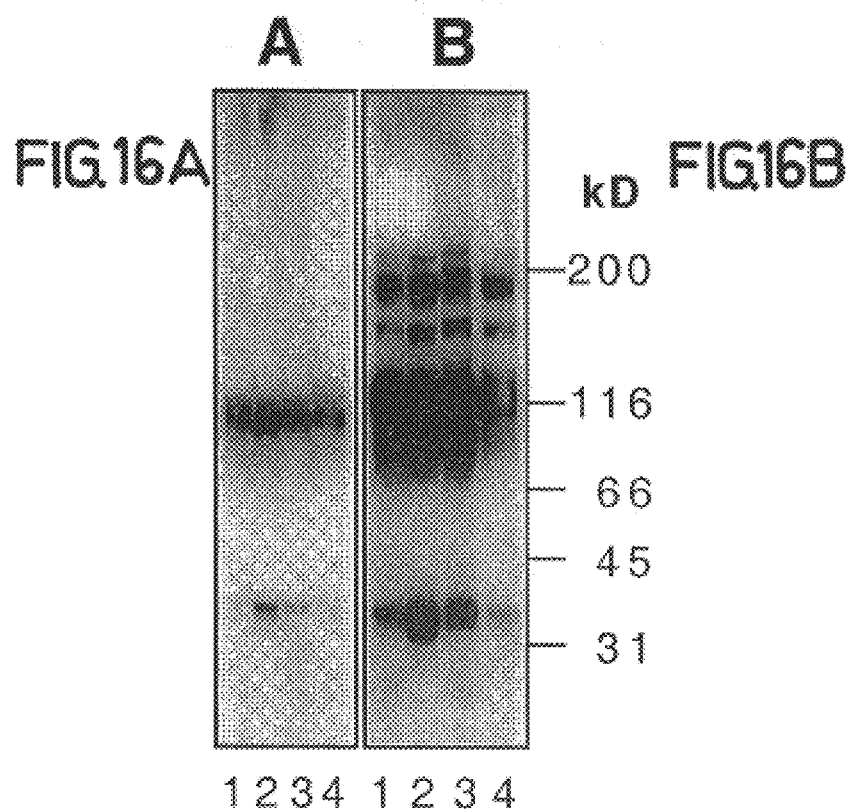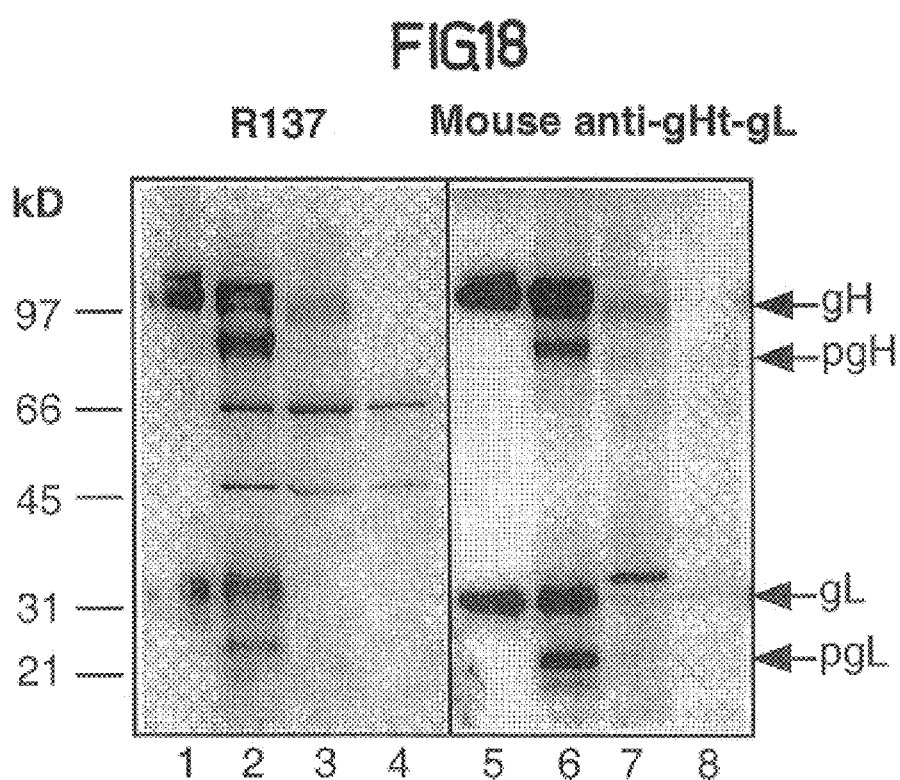

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO: 1:

Cys Thr Ala Gly Tyr Arg
1             5

(2) INFORMATION FOR SEQ ID NO: 2:

(i) SEQUENCE CHARACTERISTICS:
      (A) LENGTH: 6 amino acids
      (B) TYPE: amino acid
      (C) STRANDEDNESS: single
      (D) TOPOLOGY: linear

```
        (ii) MOLECULE TYPE: protein (iii) HYPOTHETICAL: NO (iv) ANTI-SENSE: NO (xi) SEQUENCE DESCRIPTION: SEQ ID NO: 2:

Cys Thr Ala Cys Arg Tyr
1               5

(2) INFORMATION FOR SEQ ID NO: 3:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 3:

TGCTCTAGAG CGCTATGGGG ATTTTGGGT                                       29

(2) INFORMATION FOR SEQ ID NO: 4:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 4:

TGCTCTAGAG GTTTCCGTCG AGGCATCGT                                       29
```

SOLUBLE HERPESVIRUS GLYCOPROTEIN COMPLEX VACCINE

CROSS REFERENCE TO RELATED APPLICATIONS

This application is a divisional of U.S. application Ser. No. 08/904,484, filed on Jul. 31, 1997, now U.S. Pat. No. 6,156,319 which in turn is a continuation-in-part of U.S. application Ser. No. 08/280,442, filed on Jul. 25, 1994 (now U.S. Pat. No. 5,807,557).

GOVERNMENT SUPPORT

Portions of this invention were made using funds from the U.S. Government (Public Service Health Grant Nos. NS-30606 from the National Institute of Neurological Diseases and Stroke, AI-18289 from the National Institute of Allergy and Infectious Diseases, and DE-08239 from the National Institute of Dental Research) and the U.S. Government may therefore have certain rights in the invention.

FIELD OF THE INVENTION

This invention is directed to herpesvirus vaccines.

BACKGROUND OF THE INVENTION

Herpesviruses are ubiquitous viruses which are the causative agents of numerous diseases in both humans and animals. These viruses are enveloped double stranded icosahedral DNA containing viruses, which envelope is acquired by budding of the nucleocapsid through the inner nuclear membrane. Members of the herpesvirus family which are important human pathogens include herpes simplex virus type 1 (HSV-1), herpes simplex virus type 2 (HSV-2), varicella zoster virus (VZV), Epstein Barr virus (EBV), cytomegalovirus (CMV), and human herpesviruses type 6, type 7 and type 8 (HHV-6, HHV-7 and HHV-8).

The genome of HSV-1 encodes several glycoproteins which are important for viral pathogenesis. Four glycoproteins glycoprotein B (gB), glycoprotein D (gD), glycoprotein H (gH) and glycoprotein L (gL) are essential for virus infectivity in cells in culture and each appears to play a role in the mechanism by which the virus enters cells (Roop et al., 1993, J. Virol. 67:2285). Glycoprotein H is a 110 kDa protein encoded by the UL22 open reading frame of HSV-1 (Gompels and Minson, 1986, Virology 153:230). When gH is expressed in mammalian cell systems in the absence of other HSV-1 proteins it remains within the cell as an incompletely processed molecule (Foa-Tomasi et al., 1991, Virology 180:474; Roberts et al., 1991, Virology 184:609). When gH is expressed in cells which also express gL, gH and gL form a stable complex wherein fully processed gH is evident (Hutchinson et al., 1992, J. Virol. 66:2240). In addition, cells infected with a gL-negative mutant produce virus particles which lack both gH and gL (Roop et al., 1993, J. Virol. 67:2285). However, since transport of gH to the surface of cells is reported to occur in the absence of gL, gL may not be required in some systems for correct processing and transport of gH (Ghiasi et al., 1991, Virology 185:187).

A recombinant vaccinia virus expressing both gH and gL has been used to examine whether the gH-gL complex was capable of eliciting a protective immune response in mice. Weak levels of HSV-1 specific neutralizing antibody were evident in mice containing the complex and virus clearance from the site of challenge was only marginally enhanced when the gH-gL complex was administered to the animals compared with administration of gH alone (Browne et al., 1993, J. Gen. Virol. 74:2813).

Currently, there are no effective herpesvirus vaccines available for immunization of humans against any of the plethora of diseases caused by these pathogens, although subunit preparations comprising glycoprotein B, glycoprotein D, either alone or in combination are currently in clinical trials. Since herpesviruses cause recurrent and frequently fatal or permanently debilitating infections in humans and in other animals, there is a long felt need for such vaccines.

SUMMARY OF THE INVENTION

The invention relates to a vaccine comprising a soluble herpes simplex virus gHt-gL complex suspended in a pharmaceutically acceptable carrier.

In one aspect, the herpes simplex virus is selected from the group consisting of herpes simplex virus type 1 and herpes simplex virus type 2. Preferably, the herpes simplex virus is herpes simplex virus type 1.

In one embodiment, gHt is from a herpes simplex virus selected from herpes simplex virus type 1 and herpes simplex virus type 2.

In another embodiment, the gL is from a herpes simplex virus selected from herpes simplex virus type 1 and herpes simplex virus type 2.

In yet another embodiment, the gHt is from herpes simplex virus type 1 and comprises amino acid residues selected from the group consisting of 1–792, 1–648, 1–475, 1–324 and 1–275.

In a further embodiment, the gHt is herpes simplex virus type 1 gHt comprising amino acids 1–324.

In another embodiment, the gHt is herpes simplex virus type 1 gHt comprising amino acids 1–792 and the gL is herpes simplex virus type 1 gL comprising amino acids 1–168.

The vaccine of the invention may further include a substantially pure preparation of at least one of a herpes simplex virus gD, gB or gC.

Also included in the invention is a vaccine comprising an isolated DNA encoding a soluble herpes simplex virus gHt-gL complex suspended in a pharmaceutically acceptable carrier.

In one embodiment of this aspect of the invention, the vaccine includes an isolated DNA encoding at least one of a herpes simplex virus gD, gB or gC.

The invention also relates to a herpes simplex virus neutralizing antibody which specifically binds to a soluble herpes simplex virus gHt-gL complex.

The invention further relates to an isolated DNA encoding a herpes simplex virus neutralizing antibody which specifically binds to a soluble herpes simplex virus gHt-gL complex.

There is also included in the invention a method of immunizing a human patient against a herpes simplex virus infection comprising administering to the patient a vaccine comprising a soluble herpes simplex virus gHt-gL complex suspended in a pharmaceutically acceptable carrier.

The invention further relates to a method of immunizing a human patient against a herpes simplex virus infection comprising administering to the patient a vaccine comprising an isolated DNA encoding a soluble herpes simplex virus gHt-gL complex suspended in a pharmaceutically acceptable carrier.

Also included in the invention is a method of treating a herpes simplex virus infection in a human patient comprising administering to the patient a vaccine comprising a soluble herpes simplex virus gHt-gL complex suspended in a pharmaceutically acceptable carrier.

The invention further includes a method of treating a herpes simplex virus infection in a human patient comprising administering to the patient a vaccine comprising an isolated DNA encoding a soluble herpes simplex virus gHt-gL complex suspended in a pharmaceutically acceptable carrier.

In each of the aforementioned methods of immunizing a human patient or of treating a herpes simplex virus infection in a human patient, the methods should be construed to optionally include the administration of a substantially pure preparation of at least one of a herpes simplex virus gD, gB or gC, or the administration of an isolated DNA encoding at least one of a herpes simplex virus gD, gB or gC.

There is further provided a method of treating a herpes simplex virus infection in a human patient comprising administering to the patient a herpes simplex virus neutralizing antibody which specifically binds to a soluble herpes simplex virus gHt-gL complex wherein the antibody is suspended in a pharmaceutically acceptable carrier.

Also included is a method of treating a herpes simplex virus infection in a human patient comprising administering to the patient an isolated DNA encoding a herpes simplex virus neutralizing antibody which specifically binds to a soluble herpes simplex virus gHt-gL complex, wherein the DNA is suspended in a pharmaceutically acceptable carrier.

In addition, the invention relates to a preparation of a soluble herpes simplex virus gHt-gL complex and a substantially pure preparation of a soluble herpes simplex virus gHt-gL complex.

In a preferred embodiment, the herpes simplex virus is selected from the group consisting of herpes simplex virus type 1 and herpes simplex virus type 2. Preferably, the herpes simplex virus is herpes simplex virus type 1.

In one aspect, the complex is suspended in a pharmaceutically acceptable carrier.

In another aspect, the gHt comprises amino acid residues selected from the group consisting of 1–792, 1–648, 1–475, 1–324 and 1–275.

In yet another aspect, the gHt comprises amino acids 1–324.

In another aspect, the gHt comprises amino acids 1–792 and the gL comprises amino acids 1–168.

The invention further relates to a cell, the DNA of the cell encoding a soluble herpes simplex virus gHt-gL complex.

In one aspect, the cell is HL-7.

There is also provided in the invention a method of modifying a cell to render it capable of secreting a soluble herpes simplex virus gHt-gL complex comprising introducing into the cell DNA encoding a truncated form of herpes simplex virus gH being gHt and full length herpes simplex virus gL, wherein the gHt and the gL are expressed in and secreted from the cell.

In one embodiment, the gHt comprises herpes simplex virus type 1 gH comprising amino acid residues selected from the group consisting of 1–792, 1–648, 1–475, 1–324 and 1–275.

The invention further relates to an isolated DNA comprising DNA encoding a herpes simplex virus gHt and a substantially full length herpes simplex virus gL.

BRIEF DESCRIPTION OF THE DRAWINGS

FIG. 2 comprising

FIG. 3, comprising FIGS. 3A and 3B, is a series of photomicrographs depicting intracellular localization of gH. L cells transfected with pCMV3gH-1 (FIG. 3A) or cotransfected with pCMV3gH-1 and pCMV3gL-1 (FIG. 3B)) were processed for immunofluorescence and were reacted with the gH MAb 37S, an antibody capable of reacting with gH irrespective of its conformation.

FIG. 4, comprising FIGS. 4A–4F, is a series of photomicrographs depicting analysis of cell surface expression of gH and gL. L cells cotransfected with pCMV3gH-1 and pMMTVgL-1 were incubated in the presence (Dex+) or absence (Dex−) of 1 $\mu$M dexamethasone (FIGS. 4A and 4B, or FIG. 4C and 4D, respectively). In FIGS. 4E and 4F, cells were cotransfected with pCMV3gH-1 and pCMV3gL-1. Expression of gH was detected using the gH MAb 37S and anti-mouse IgG fluorescein-labeled conjugate (FIGS 4A, 4C and 4E). Expression of gL was detected using rabbit anti-gL serum and anti-rabbit IgG rhodamine-labeled conjugate.

FIG. 5, comprising FIGS. 5A–5F is a series of photo micrographs depicting cellular localization of gL. L cells were transfected as follows: pCMV3gL-1 alone (FIGS. 5A and 5B); pCMV3gL-1 plus pCMV3gH(792) (FIGS. 5C and 5D); or, pCMV3gL-1 plus pCMV3gH-1 (FIGS. 5E and 5F). Expression of gL was detected using anti-gL serum and fluorescein-labeled conjugate. Cells in FIGS. 5A, 5C and 5E were fixed with acetone to examine internal localization of gL. Cells in FIGS. 5B, 5D and 5F were not fixed in order to examine cell surface expression of gL.

FIG. 6 is a photograph of a gel containing immunoprecipitated gL to determine whether gL is secreted from cells. L cells were transfected with the following plasmids: pCMV3gL-1 alone; pCMV3gL-1 plus pCMV3gH(792); or, pCMV3gL-1 plus pCMV3gH-1. Transfected cells were incubated in the presence of $^{35}$S-labeled cysteine. Supernatants were collected from cells so incubated, which supernatants were concentrated and immunoprecipitated with anti-gL serum. Immunoprecipitated proteins were resolved by SDS-PAGE. Abbreviations: gL, pCMV3gL-1; gH(792), pCMV3gH(792); gH, pCMV3gH-1.

FIG. 7 is a photograph of a gel depicting analysis of cell supernatants for the presence or absence of secreted gL and gH(792). L cells were transfected with pCMV3gL-1 plus pCMV3gH(792), or with pCMV3gH(792) alone. Transfected cells were incubated in the presence of $^{35}$S-labeled cysteine. Supernatants were collected from cells so incubated, which supernatants were concentrated and immunoprecipitated with either gH MAb R83 or with anti-gL serum. Immunoprecipitated proteins were resolved by SDS-PAGE. Abbreviations: L, pCMV3gL-1; H, pCMV3gH(792).

FIG. 13, comprising FIGS. 13A, 13B and 13C is a serise of images of gels depicting extracellular expression and purification of gHt-gL complex from HL-7 cells. Lane 1 of each of FIGS. 13A, 13B and 13C contained 20 µl of HL-7 cell supernatant. Lane 2 of each of FIGS. 13A, 13B and 13C contained 20 µl of flow through, and Lane 3 of each of FIGS. 13A, 13B and 13C contained 1 µg of protein eluted from the 53S immunoadsorbant column. In FIG. 13A, the samples were analyzed by electrophoresis on a 10% SDS-polyacrylamide gel. The gel was stained for protein with silver stain. In FIG. 13B, the proteins were electrophoresed on a 10% SDS-polyacrylamide gel, transferred to nitrocellulose and probed with anti-gL ascites 8H4. In FIG. 13C, the proteins were electrophoresed on a 10% SDS-polyacrylamide gel, transferred to nitrocellulose and probed with anti-gH serum R83.

FIG. 14 comprising FIGS. 14A and 14B depicts reactivity of purified gHt-gL with gH specific antibodies. FIG. 14A is an image of a gel depicting purified gHt-gL which was immunoprecipitated with either MAb LP11 (lane 1) or with αUL1–2 (lane 2) and was then electrophoresed on a 10% SDS-polyacrylamide gel. The proteins were transferred to nitrocellulose and were probed with R83 (anti-gH serum) (lane 1) or with MAb 8H4 (anti-gL) the arrow indicates heavy chain from LP11. FIG. 14B is a graph depicting reactivity of gHt-gL with selected antibodies. Various concentrations of gHt-gL were coated onto an ELISA plate for 2 hours at room temperature. Wells were reacted with anti-gH MAbs LP11 (filled squares) 53S (filled circles) or 37S (filled triangles). Binding of these antibodies was detected with horseradish peroxidase-labeled goat anti-mouse antibody and ABTS substrate.

FIG. 15, comprising

FIG. 16, comprising FIGS. 16A and 16B is an image of two gels depicting immunoblot (Western blot) analysis of serum samples from rabbits immunized with gHt-gL. FIG. 16A: Purified gHt-gL was electrophoresed on a denaturing 10% SDS-polyacrylamide gel, transferred to nitrocellulose and reacted with R136 (lane 1), R137 (lane 2), R138 (lane 3) or R139 (lane 4). FIG. 16B: Purified gHt-gL was electrophoresed on a non-denaturing (native) 10% SDS-polyacrylamide gel, transferred to nitrocellulose and reacted with R136 (lane 1), R137 (lane 2), R138 (lane 3) or R139 (lane 4).

FIG. 17, comprising FIGS. 17A and 17B is a series of graphs depicting blocking of HSV entry into cells by rabbit antibodies specific for gHt-gL. FIG. 17A: HSV-1 hrR3 was incubated for 90 minutes at 37° C. with various concentrations of rabbit anti-gHt-gL sera R136 (filled squares), R137 (filled circles), R138 (filled triangles), or R139 (filled diamonds). The serum-virus mixture was added to Vero cell monolayers in a 96 well plate, incubated at 4° C. for 90 minutes followed by incubation at 37° C. for 5 hours. Virus entry was assayed as an increase in β-galactosidase activity in cytoplasmic extracts obtained from each well and expressed as % of control values obtained with virus alone. FIG. 17B: HSV-1 hrR3 was added to Vero cell monolayers at 4° C. for 90 minutes. The medium was removed and various dilutions of either R83 (filled circles), R137 (bolded X) or LP11 (inverted, filled triangles) were added. The monolayers were incubated at 4° C. for 90 minutes followed by incubation at 37° C. for 5 hours. Virus entry was assayed as described in FIG. 17A.

FIG. 18 is an image of immunoblot (western blot) analysis of cytoplasmic extracts of HSV-1 or HSV-2 infected Vero cells. Samples of purified gHt-gL or cytoplasmic extracts were electrophoresed on a denaturing 10% SDS-polyacrylamide gel, transferred to nitrocellulose and reacted with R137 (lanes 1–4) or mouse anti-gHt-gL (lanes 5–8). The mouse serum was pooled from 9 animals immunized with gHt-gL Experiment I, Table 2). gHt-gL purified from HL-7 cells (lanes 1 and 4) were included on the gel as a control. Cytoplasmic extracts were prepared from uninfected cells (lanes 2 and 6) or from cells infected with HSV-1 (NS) (lanes 3 and 7) or HSV-2 (333) (lanes 4 and 8).

FIG. 19 is a series of graphs depicting blocking of HSV entry by mouse antibodies to gD or to gHt-gL.

DETAILED DESCRIPTION OF THE INVENTION

Figure 1:
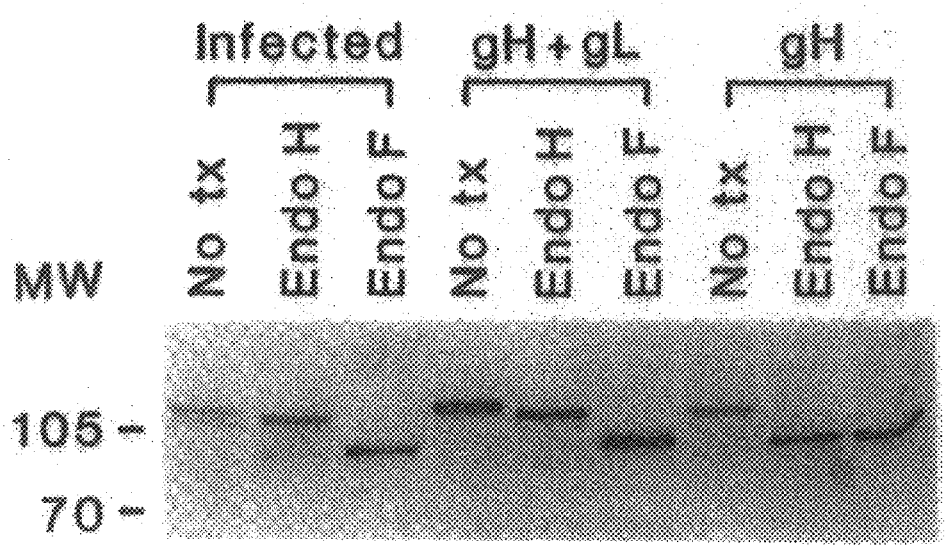
FIG. 1 is a photograph of a gel depicting analysis of carbohydrate processing in gH. Cytoplasmic extracts were prepared from HSV-1 infected L cells, or from L cells transfected with pCMV3gH-1 plus pCMV3gL-1 or with pCMV3gH-1 alone. Extracts were subsequently treated with either endo H, endo F, or were untreated and the proteins contained therein were resolved by SDS-PAGE, transferred to a nylon membrane and incubated in the presence of rabbit anti-gH serum (R83) and goat anti-rabbit horseradish peroxidase conjugate. Reacted proteins were detected using a chemiluminescent substrate. Abbreviations: gH, pCMV3gH-1; gL, pCMV3gL-1; no tx, not treated.

The invention relates to the discovery that two HSV-1 specific glycoproteins, gH and gL, when complexed together and administered to animal, serve to protect the animal against infection by HSV. Thus, there has been discovered a subunit vaccine comprising a soluble HSV-1 gHt-gL complex, which vaccine is useful not only as a prophylactic therapeutic agent for protection of an animal against a herpesvirus infection, but is also useful as a therapeutic agent for treatment of an ongoing herpesvirus infection in an animal, particularly in an animal having a high propensity to reactivate a herpesvirus infection.

It is known that HSV-1 gH and gL form a molecular complex which is present on the virion envelope. This complex is essential for viral infectivity in that it is required for entry of virus into cells and for cell to cell spread of virus which is believed to occur via membrane fusion. In the experiments described herein, gH and gL have been stably expressed in and secreted from mammalian cells in culture as a soluble complex, named gHt-gL. This complex, when inoculated into an animal, elicits antibody which serves to neutralize virus in a virus neutralization cell culture assay. Further, when the gHt-gL complex is inoculated into an animal, it elicits an immune response which serves to protect the inoculated animal against disease when the animal is challenged with infectious virus. Thus, it has been discovered according to the present invention that a soluble herpes simplex virus type 1 gHt-gL complex functions to vaccinate an animal against herpes simplex virus disease.

By the term "soluble gHt-gL complex" as used herein, is meant a complex comprising a truncated HSV gH and a substantially full length HSV gL which are bound together in the complex and which are soluble in an aqueous solution.

The soluble gHt-gL complex of the invention may be obtained in large quantities for use as a vaccine for protection of humans against HSV infection, or for eliminating or diminishing the frequency of reactivation of the virus from the latent state thus, reducing the severity of recurrent HSV infection in humans. The complex is also useful as a diagnostic reagent for assessing the presence or absence of a herpesvirus infection in a human. Such an assessment is made by obtaining serum from the individual and reacting it with the complex in a standard immunoassay such as radioimmunoassay or enzyme linked immunoadsorbent assay (ELISA).

By the term "vaccine" as used herein, is meant a composition, a protein complex or a DNA encoding a protein complex which serves to protect an animal against a herpesvirus disease.

By the term "immunizing a human against herpes simplex virus infection" is meant administering to the human a composition, a protein complex, a DNA encoding a protein complex, an antibody or a DNA encoding an antibody, which elicits an immune response in the human which immune response provides protection to the human against a herpes simplex virus disease.

Homologs of the genes encoding HSV-1 gH and gL have been identified in most other herpesviruses including human CMV (Cranage et al., 1988, J. Virol. 62:1416), VZV (Davison and Scott, 1986, J. Gen. Virol. 67:1759) and EBV (McGeoch and Davison, 1986, Nucl. Acids Res. 4:4281). The CMV UL115 gene, a positional homolog of the HSV-1 gL gene, encodes a secreted protein which forms a complex with CMV gH and is therefore a positional and likely functional (although not a sequence) homolog to HSV-1 gL (Kaye et al., 1992, J. Gen. Virol. 73:2693; Spaete et al., 1993, Virology 193:853). HHV-6 (Josephs et al., 1991, J. Virol. 65:5597), pseudorabies virus (Klupp et al., 1991, Virology 182:732) and herpesvirus saimiri (Gompels et al., 1988, J. Gen. Virol. 69:2819) also each encode homologs of HSV-1 gH and gL.

The invention should not be construed to be limited to a soluble HSV-1 gHt-gL complex. Rather, the invention should be construed to encompass soluble gHt-gL complexes which are derived from both HSV-1 and HSV-2, which soluble complexes may be used as vaccines to protect humans from disease caused by either of these two types of viruses. As the data presented herein establish, antibody directed against soluble HSV-1 gHt-gL complex serves to neutralize infection of cells in culture by HSV-2. Thus, since antibodies raised against HSV-1 gHt-gL complex neutralize HSV-2, the invention should be construed to include gHt-gL complexes from either virus type which serve to protect cells and humans against infection by both HSV-1 and HSV-2.

The gHt-gL complex of the invention may therefore comprise one subunit derived from HSV-1 and another subunit derived from HSV-2, yielding at least four general classes of complexes which are encompassed by the invention. One complex comprises HSV-1 gH bound to HSV-1 gL. Another complex comprises HSV-1 gH bound to HSV-2 gL. A third complex comprises HSV-2 gH bound to HSV-1 gL and a fourth complex comprises HSV-2 gH bound to HSV-2 gL.

The gHt-gL complex of the invention comprises a truncated gH molecule which is complexed to a substantially full length gL molecule. It has been discovered in the present invention that it is necessary that the gH portion of the gHt-gL complex be truncated in order that the complex is secreted from the cell in soluble form. Truncated forms of gH (referred to herein as "gHt") include those containing amino acid residues selected from the group consisting of 1–792, 1–648, 1–475, 1–324 and 1–275.

As is customary in the field of herpes simplex virology, amino acids in proteins encoded by herpes simplex viruses are numbered from the first methionine in the protein.

By the term "truncated" as used herein as it refers to gH, is meant a molecule of gH which contains less than the complete number of amino acids found in a wild type protein. Particularly, the term truncated is used to mean a gH molecule which is not membrane anchored, i.e., which comprises a deletion or other mutation which facilitates secretion of gH from the cell. Mutations in the gH molecule which give rise to different lengths of gH may comprise insertion, deletion or point mutations. An insertion mutation is one where additional base pairs are inserted into a DNA molecule. A deletion mutation is one where base pairs have been removed from a DNA molecule. A point mutation is one where a single base pair alteration has been made in a DNA molecule. Each of these mutations is designed such that creation of any one of them in a DNA molecule effects an alteration in the nature of any polypeptide expressed by that DNA, which alteration results in a gH molecule capable of binding to gL to form a complex having biological activity as defined herein, and which gH-gL complex is secreted from a cell in which it is expressed.

The complex also includes a substantially full length gL molecule which may comprise all of the amino acids of gL, or may also be mutated comprise less than all of the amino acids of gL.

By the term "substantially full length herpesvirus gL" as used herein, is meant a herpesvirus gL molecule which comprises a sufficient number of amino acids so that the substantially full length gL is capable of binding to gHt, forming a complex therewith, which complex has biological activity as defined herein. Thus, a substantially full length gL molecule does not necessarily contain all of the amino acids which comprise herpesvirus gL, (although according to the invention, it may) but rather, the molecule comprises a substantial portion of the molecule sufficient for binding to gHt and forming a biologically active complex therewith.

Referring to gH and gL molecules encoded by HSV-1, it has been discovered in the present invention that a stable gHt-gL complex can be formed wherein the gHt component comprises amino acids 1–324 and the gL component is substantially fill length. A stable gHt-gL complex can also be formed wherein the gHt component comprises amino acids amino acids 1–792 and the gL component comprises amino acids 1–168. Thus, the invention should not be construed to be limited to any particular specific length of either gH or gL. Rather, the invention should be construed to encompass any length of a truncated gH which binds to any length of gL to form a complex which has gHt-gL biological activity as defined herein. The procedures which are used to generate plasmids expressing proteins of different lengths are well known in the art and the means for expressing gH and gL in a cell such that they form a biologically active complex are described in detail herein. Thus, it is well within the skill of those in the art to generate biologically active gHt-gL complexes, wherein the gHt-and gL each comprise an animo acid length which is different from the gHt and gL molecules disclosed in the experimental examples section herein.

The invention should also be construed to include any form of a gHt-gL complex having substantial homology to the HSV-1 gHt-gL complex disclosed herein. Preferably, a gHt-gL complex which is substantially homologous is about 50% homologous, more preferably about 70% homologous, even more preferably about 80% homologous and most preferably about 90% homologous to the gHt-gL complex secreted from HL-7 cells.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC 5' and 3'TAAGCC 5' share 50% homology. Also by way of example, the amino acid sequences CTAGYR and CTACRY (SEQ ID Nos: 1 and 2, respectively) share 50% homology.

To generate an HSV gHt-gL complex, following the teaching provided herein it is well within the skill of those in the art to take a plasmid encoding truncated gH and full length gL from other strains of HSV-1 and introduce it into a population of mammalian cells such that the cells become stably transfected with the plasmid and are caused to express and secrete a soluble form of gHt-gL complex as described herein. It is also well within the skill of those in the art to take yet another plasr nid encoding gH and gL (i.e., DNA obtained from various strains of HSV-2, which DNA encodes gH and gL) and generate cell lines which secrete soluble gHt-gL complex following the teaching contained herein.

The invention should not be construed to be limited to the particular method of introduction of herpesvirus DNA into mammalian cells described herein. Rather, other methods may be used to generate cells which express a soluble form of gH-gL complex. Such methods include, but are not limited to, the use of retroviral and other viral vectors for delivery of herpesvirus-specific gH-gL encoding DNA into cells and the use of other chemical means of transfection. In addition as described herein, the complex to be formed by cells encoding gH-gL may include a mixture of gH derived from one virus strain and gL derived from yet another virus strain. Generation of such mixed complexes is accomplished using the protocols described above and other protocols available to virologists, described for example in Sambrook et al. (1989, Molecular Cloning: A Laboratory Manual, Cold Spring Harbor, N.Y.).

The invention should also be construed to include gHt-gL complexes which are generated in mammalian cells as described herein, or which are generated by other means, such as by expression in a baculovirus system, or a yeast expression system. gHt-gL complexes which are generated by synthetic methods are also included in the invention.

Also contemplated by the invention is a subunit vaccine comprising an isolated nucleic acid, preferably, an isolated DNA, encoding a gHt-gL complex. Such a nucleic acid, preferably, a DNA molecule, may be used directly as a vaccine as described herein, or it may be used to transfect cells in order to produce large quantities of gHt-gL for use as a subunit vaccine.

To generate a DNA encoding gHt-gL, the desired gHt and gL coding sequences are ligated together in either of two configurations. In the first configuration, a plasmid is generated having the following elements: a promoter for expression of gHt which is positioned upstream of a desired gHt encoding sequence and a promoter for expression of gL which is positioned upstream of a desired gL coding sequence. The plasmid therefore encodes gHt and gL on the same molecule wherein expression of each of gHt and gL is under the control of an individual promoter sequence, preferably the same promoter sequence. Both gHt and gL are expressed individually from:this plasmid in a cell and form complex therein which is secreted from the cells as described herein.

Alternatively, a plasmid may be generated which has the following elements: a single a promoter which is positioned upstream of a desired gHt encoding and a desired gL encoding sequence, the gHt and gL encoding sequences being separated by a DNA sequence encoding a cleavage site for a protease. In this plasmid, the gHt and gL encoding sequences may be positioned in the plasmid in either orientation which respect to each other, such that either one of them is juxtaposed to the promoter sequence. DNA encoding the protease cleavage site which is positioned between the gHt and gL coding sequences may be any DNA known to encode a length of amino acids which are cleaved by any protease which is present in a majority of cells and which is particularly present in cells into which the DNA of the invention is introduced. gHt-gL which is expressed by this plasmid is initially expressed in a cell as a single length of protein comprising gHt and gL fused together via a protease cleavage site. Subsequent cleavage of the fused protein by a protease generates individual molecules of gHt and gL which form a complex which is secreted from the cell as desccribed herein.

The isolated DNA of the invention is not limited to a plasmid based DNA, but rather may include any form of DNA which encodes gHt-gL as described herein in the case of a plasmid DNA. Thus, the isolated DNA of the invention may include a viral vector, a non-viral vector, or a plasmid DNA.

The promoter sequence which is used to drive expression of gHt-gL in either type of configuration may be any constitutive promoter which drives expression of these proteins in cells. Such promoters therefore include, but are not limited to, the cytomegalovirus immediate early promoter/regulatory sequence, the SV40 early promoter/enhancer sequence, the Rous sarcoma virus promoter/enhancer and any other suitable promoter which is available in the art for constitutive expression of high levels of proteins in cells.

When the isolated DNA of the invention is used to generate large quantities of gHt-gL complex, cells are transfected with the DNA using the methodology disclosed herein or any other available transfection methodology, gHt-gL is expressed and is recovered from the cells as described herein.

When the isolated DNA is to be used as a vaccine, a DNA based vaccine is prepared following the disclosure described in Wang et al. (1993, Proc. Natl. Acad. Sci. USA 90:4156–4160). The vaccine comprises DNA encoding a gHt and a substantially fill length gL expressed under the control of any of the promoters disclosed herein. Antibodies are raised against the expressed protein by intramuscular injection of DNA into the hind limb of six to eight week old mice. The anesthetic bupivacaine (50 $\mu$l of a 0.5% solution) is used to improve immunogenicity of the vaccine. The animals are immunized first with bupivacaine and then are immunized the following day with 50 $\mu$g of plasmid DNA encoding gHt-gL. At about four weeks, animals are test bled to measure the level of anti-gHt-gL antibody and are re-injected with bupivacaine and DNA on successive days. On day 45, or thereabouts, serum is collected from the animals and is tested to determine whether antibodies contained therein neutralize virus in the virus neutralization assays described herein. DNA encoding other HSV glycoproteins such as, but not limited to gD, gC and gB may included for immunization of the animal using the same protocol.

To adapt this DNA based vaccine to human subjects, the amounts of DNA, the route of injection and the adjuvants to be used may vary from that just described. However, these variations will be readily apparent to the skilled artisan working in the field of DNA based vaccines.

The invention should be construed to include any and all isolated DNAs which are homologous to the gHt-gL DNA described and referenced herein, provided these homologous DNAs have the biological activity of gHt-gL complex as defined herein.

An "isolated DNA", as used herein, refers to a DNA sequence, segment, or fragment which has been purified from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to DNA which has been substantially purified from other components which naturally accompany the DNA, e.g., RNA or DNA or proteins which naturally accompany it in the cell.

The invention should also be construed to include DNAs which are substantially homologous to the DNA isolated according to the method of the invention. Preferably, DNA which is substantially homologous is about 50% homologous, more preferably about 70% ho mnologous, even more preferably about 80% homologous and most preferably about 90% homologous to DNA obtained using the method of the invention.

The invention should therefore be construed to include any form of a gHt-gL complex or DNA encoding a gHt-gL complex, which is homologous to the HSV-1 gHt-gL complex or it's DNA disclosed herein and which has or encodes gHt-gL complex biological activity as defined herein.

To purify a gHt-gL complex for use as a vaccine or other therapeutic, the examples given in the experimental details section may be followed. Essentially, a substantially pure preparation of a gHt-gL complex is obtained by immunoaffinity chromatography of supernatants obtained from cells which express and secrete gHt-gL complex using the monoclonal antibody (MAb), 53S or any other antibody which specifically binds gH, gL or the combination of the two. To purify the gH-gL complex, the supernatant is passed over an affinity column comprising anti-gHt-gL complex antibody, the column is washed with buffer and adsorbed proteins are eluted from the column in fractions using an elution buffer, such as 50 mM glycine buffer (pH 2.5) containing 0.5 M NaCl and 0.1% Triton X-100. Fractions so elute a are neutralized with a high pH buffer, for example, Tris-HCl, pH 9.0 and are then analyzed for the presence of gHt and gL by gel electrophoresis or other protein detection technology. Fractions containing the proteins are pooled and are concentrated using a commercially available concentrator, for example, a Centricon-10 concentrator.

By the term "substantially pure" as it refers to a gH-gL complex, is meant a complex which has been separated from the components which naturally accompany it in the cell or medium in which it resides. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g, in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

The invention should be construed to include modifications of gHt or gL which in their modified form are capable of forming a complex having the biological activity of the gHt-gL complex disclosed herein. For example, conservative amino acid substitutions may be made in either or both of gHt or gL which alter the primary sequence of the proteins without significantly affecting the ability of these proteins to bind together and retain the biological activity of the gHt-gL complex. Conservative amino acid substitutions typically include substitutions within the following groups, but are not limited to these groups: glycine, alanine; valine, isoleucine, leucine; aspartic acid, glutamic acid; asparagine, glutamine; serine, threonine; lysine, arginine; phenylalanine, tyrosine. Also included are proteins and peptides which have been modified using ordinary molecular biological techniques so as to improve their resistance to proteolytic degradation, to optimize solubility properties, or to alter post-translational modification of the protein or peptide. The proteins and peptides of the invention are not limited to products of any of the specific exemplary processes listed herein.

By "biological activity" of gHt-gL as used herein, is meant a gHt-gL complex which when inoculated into an animal elicits an antibody, a virus neutralizing antibody, which neutralizes the infectivity of a herpesvirus in a virus neutralization assay and which protects an animal against disease when wild type virus is subsequently administered to the animal.

Typically, a virus neutralization assay involves incubation with a known titer of infectious virus of serial dilutions of serum obtained from an animal administered the vaccine for a period of time. Following the incubation period, the amount of infectious virus remaining is quantitated, usually by plaque assay.

The term "virus neutralizing effective amount" as used herein, means an amount of antigen which elicits an immune response when administered to an animal, which response is capable of neutralizing virus infectivity to a level which is less than 50% of normal infectivity in a standard virus neutralization assay.

A virus neutralizing immune response is also one which affords protection to the animal from lethal challenge with wild type virus. Protection against lethal challenge with wild type virus is typically assessed by first immunizing a series of animals with the subject antigen to generate serum capable of neutralizing virus infectivity in a standard virus neutralization assay. The animals are then inoculated with a serial dilutions of wild type virus, which dilutions contain sufficient virus to kill non-immunized animals. The death rate of the animals is quantitated and is compared to the level of the virus neutralizing immune response in each of the animals. Protection from lethal challenge has been effected when non-immunized animals die and immunized animals do not die as a result of infection with virus.

Also included in the term "virus neutralizing immune response" is a response which affords protection against HSV disease, such as zosteriform disease, the establishment of latency in ganglia that innervate the site of infection and the production of subclinical (asymptomatic) virus shedding. Protection against HSV disease is typically assessed by counting HSV lesions that develop at the site of virus challenge, or by scoring animals for erythema (redness) and swelling. In the zosteriform model, disease is scored as primary, i.e., at the site of infection, or secondary, ie., at a site remote from the initial site of infection but along the axis of the same dermatome.

Protection against the establishment of latency is typically assessed by removing the ganglia and determining the presence (and amount) or absence of HSV in the ganglia. Protection against subclinical virus shedding is typically determined by culturing virus from the animal at selected intervals post-challenge or by using standard PCR to measure levels of viral DNA.

By the term "virus neutralizing antibody" as used herein, is meant a reduction in the infectivity of a virus in the presence of the antibody compared with the infectivity of the virus in the absence of the antibody. Typically, an antibody is a virus neutralizing antibody when the infectivity of the virus is reduced by about 50% in the presence of the antibody at a dilution of the serum containing the antibody which is greater than 1:20. The higher the dilution of serum which neutralizes a constant amount of virus by 50%, the greater the estimate of the activity of the antibody contained within the serum.

The term "protect an animal against disease" is used herein to mean a reduction in the level of disease caused by a wild type virus in an animal inoculated with a gHt-gL complex compared with the level of disease caused by a wild type virus in an animal which as not been inoculated with a gHt-gL complex. As the data presented herein establish, the gHt-gL complex of the invention protected an animal against infection by HSV to the same extent as did gD when animals were similarly administered this glycoprotein. As noted herein, HSV gD as a subunit vaccine is currently in clinical trials and at present represents the "gold standard" of HSV vaccines. Thus, the gHt-gL subunit vaccine of the invention is capable of protecting an animal against HSV disease to a level at least as good as that observed when gD is used to immunize an animal.

To determine whether a gHt-gL complex generated using the methods described herein has biological activity, the following general protocols are followed. To assess biological activity of a gHt-gL complex, an animal is first immunized with the complex. Although the examples provided herein are directed to rabbits and mice, any other animal may be used. .

Using mice as an example, a mouse is immunized at about biweekly intervals with about four doses of approximately 10 $\mu$g of gHt-gL per dose. Serum obtained from the mouse post-immunization is tested for the presence of an anti-gHt-gL complex antibody in any immunological assay, for example, an ELISA. A virus neutralization assay is performed wherein dilutions of serum obtained from the immunized animal are mixed with infectious virus. The mixture is added to cells and neutralization of virus by the antibody is measured as described herein.

To determine the efficacy of the gH-gL complex as a vaccine, the gH-gL complex is administered intraperitoneally to mice using an adjuvant system suitable for administration of proteins to mice, for example, the Ribi adjuvant system (RAS; Ribi Immunochemical Research, Hamnilton, Mont.), or other suitable adjuvant. Both pre- and post-immune serum is obtained from the mice and the presence or absence of antibodies is determined in the standard assays described herein. The ability of anti-gHt-gL antibodies to neutralize HSV is determined in a standard viral neutralization assay, such as but not limited to, a plaque reduction neutralization assay. Mice are administered a range of concentrations of gH-gL complex from about 0.1 to about 20 μg per dose, using several different immunization schedules, i.e., weekly, biweekly, in order to determine the optimum conditions for effective immunization of the mice against HSV. Sera obtained from mice so immunized are tested for the ability to neutralize HSV-1 strain NS (or other strain of HSV depending on the virus from which the gHt-gL complex is derived) and other strains of both HSV-1 and HSV-2. Since the ability of an antibody to neutralize virus in culture is predictive of the protective activity of that antibody, neutralization of any one of the viruses listed above by antibody raised against the gHt-gL complex is predictive of the ability of gHt-gL complex to serve as a subunit vaccine candidate against that virus.

To assess whether antibody raised against gH-gL protects mice against in vivo challenge with virus, immunized and non-immunized mice are administered various concentrations of virus intraperitoneally at a time post-immunization when peak antibody levels are apparent following the experiments described above. The number of immunized animals which survive challenge by virus is indicative of the efficacy of the gHt-gL complex as a vaccine candidate. Although these studies may be conducted using an intraperitoneal route, studies on the vaccine capabilities of a gHt-gL complex may involve all possible routes of administration including, but not limited to, intramuscular, subcutaneous and even oral routes of administration. In addition, as described in the experimental details section herein, other animal models for herpesvirus infections, such as guinea pigs are used.

Furthermore, studies may be conducted to examine viral latency in gH-gL immunized animals surviving virus challenge and in animals which are administered the complex and are then tested in any of the available latency models of HSV infection. Such studies will be performed according to published protocols, such as that described by Stanberry (Pathogenesis of herpes simplex virus infection and animal models for its study. In: Current Topics in Microbiology and Immunology, 179: Herpes simplex virus: Pathogenesis and Control, Springer Verlag (Berlin), 1992, pp 15–30). Thus, the establishment of latency in ganglia that innervate the site of infection and the production of subclinical (asymptomatic) virus shedding may be examined as described herein.

The subunit vaccine of the invention may be formulated to be suspended in a pharmaceutically acceptable composition suitable for use in animals and in particular, in humans. Such formulations include the use of adjuvants: such as muramyl dipeptide derivatives (MDP) or analogs which are described in U.S. Pat. Nos. 4,082,735; 4,082,736; 4,101, 536; 4,185,089; 4,235,771; and, 4,406,890. Other adjuvants which are useful include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606, 918).

The subunit vaccine of the invention may be encapsulated into liposomes for administration to the animal. See for example, U.S. Pat. Nos. 4,053,585, 4,261,975 and 4,406, 890.

The subunit vaccine of the invention is administered to a human by any suitable route of administration, for example, subcutaneously, intramuscularly, orally, intravenously, intradermally, intranasally or intravaginally. The complex is first suspended in a pharmaceutically acceptable carrier which is suitable for the chosen route of administration and which will be readily apparent to those skilled in the art of vaccine preparation and administration. The dose of vaccine to be used may vary dependent upon any number of factors including the age of the individual and the route of administration. Typically, the subunit vaccine is administered in a range of 1 μg to 50 mg of protein per dose. Approximately 1–10 doses are administered to the individual at intervals ranging from once per day to once per week to once every few years.

The vaccine of the invention is useful for prevention of herpesvirus disease in an animal, preferably a human. However, the vaccine is also useful as a therapeutic agent for treatment of acute episodes of herpesvirus infection in order to boost the immune response in the animal. Thus the invention contemplates both prophylactic and therapeutic uses for the vaccine of the invention.

It should be appreciated that the subunit vaccine of the invention may be combined with other subunit vaccines, such as subunit vaccines comprising gD, gB or combinations thereof, gC, and the like each of which may be generated and used according to published protocols and the procedures described herein.

The antibodies which are produced in animals may themselves serve as therapeutic compounds for treatment of HSV infection, particularly in severely immunocompromised individuals, such as those infected with human immunodeficiency virus or those receiving transplants. The antibody may also be useful for administration to newborn infants infected with HSV and to adults at risk for developing HSV encephalitis. The invention should therefore be construed to include anti-gHt-gL antibodies as described herein and anti-gHt-gL antibodies which may be modified such that they are phage displayed and/or humanized using technology available in the art. It will be appreciated that the antibodies which are useful include those which specifically bind to a gHt-gL complex derived from either HSV-1 or HSV-2 and a gHt-gL complex wherein one component id derived from HSV-1 and the other component is derived from HSV-2. Similarly, DNA encoding antibodies which are now described may comprises DNAs encoding gHt and gL subunits derived from either of HSV-1 or HSV-2.

The generation of polyclonal and monoclonal antibodies is well known in the art and is described and referenced herein. Phage displayed and humanized antibodies are also well known in the art and are also described herein.

Given the advances in technology in cloning DNA encoding proteins comprising antibodies, the invention should also be construed to include an isolated DNA which encodes a gHt-gL antibody, or a portion or fragment of such antibody.

When the antibody of the invention is a monoclonal antibody, the nucleic acid encoding the antibody may be cloned and sequenced using technology which is available in the art, and is described, for example, in Wright et al. (1992, Critical Rev. in Immunol. 12(3,4):125–168) and the references cited therein. Further, the antibody of the invention may be "humanized" using the technology described in Wright et al., (supra) and in the references cited therein.

For example, to generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, *Molecular Cloning: A Laboratory Manual*, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, *Adv. Immunol.* 57:191–280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

By the term "specifically binds," as used herein, is meant an antibody which recognizes and binds an HSV gHt-gL complex, but does not substantially recognize or bind other molecules in a sample.

The invention thus includes an isolated DNA encoding a gHt-gL antibody or a portion of the antibody of the invention. To isolate DNA encoding an antibody, for example, DNA is extracted from antibody expressing phage obtained according to the methods of the invention. Such extraction techniques are well known in the art and are described, for example, in Sambrook et al. (supra).

The anti-gHt-gL complex antibody of the invention may be conventionally administered to a mammal, preferably a human, parenterally, by injection, for example, subcutaneously, intravenously, intramuscularly, and the like. Additional formulations which are suitable for other modes of administration include suppositories, intranasal aerosols and, in some cases, oral formulations. The antibody may be administered in any of the described formulations either daily, several times daily, weekly, bi-weekly or monthly or several times a year in a dosage which will be apparent to the skilled artisan and will depend on the type of disease being treated. Preferably, the dosage will range from about 1 nanogram of antibody to several milligrams of antibody to even up to about 100 milligrams of antibody per dose.

It will be appreciated that the subunit vaccine of the invention, the DNA vaccine of the invention and the antibody of the invention may be used to prevent or treat HSV infections in a human in cases where the human is not yet infected, in cases where the human is infected and treatment is initiated in order to prevent more severe infection, such as, for example, HSV encephalitis, and in cases where the human is latently infected with the virus and has a high propensity to reactivate. In addition, the compositions of the invention are useful for treatment of neonates at risk for developing severe herpesvirus infection and immunosuppressed individuals at risk for developing severe herpes virus infection, such as is the case in patients having acquired immunodeficiency syndrome and in transplant patients and those requiring chemotherapy.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

The experiments which relate to the identification and characterization of a soluble gH-gL complex are now described.

The materials and methods used in these experiments are presented below.

Cells and Viruses

Mouse Ltk$^-$ cells (L cells) were propagated in α-minimal essential medium (Gibco) supplemented with 10% heat-inactivated fetal calf serum (FCS, obtained from HyClone Laboratories), gentamicin, amphotericin B, vitamins, and N-2-hydroxyethypiperazine-N'-2-ethanesulfonic acid (HEPES) buffer solution. HSV-1 strain NS was propagated as described (Cines et al., 1982, J. Clin. Invest. 69:123).

Antibodies

Polyclonal antibodies and MAbs used in this study were as follows: rabbit polyclonal anti-gH antibody preparations R82 and R83 (Roberts et al., 1991, Virology 184:609); anti-gH MAbs include 37S (Showalter et al., 1981, Infn. Immun. 34:684), 53S (American Type Culture Collection), and LP11 (Buckmaster et al., 1984, Virology 139:408); rabbit antiserum raised against the gL UL1–2 peptide (anti-gL serum; Hutchinson et al., 1992, J. Virol. 66:2240).

Plasmids Expressing gH

Plasmid pCMV3gH-1 contains a 3.1 kb HindIII fragment obtained from pSR95 (Roberts et al., 1991, Virology 184:609), which fragment contains the entire HSV-1 strain NS gH coding region ligated into the HindIII site in the polylinker of pCMV3 (Andersson et al., 1989, J. Biol. Chem. 264:8222). Thus, plasmid pCMV3gH-1 encodes gH under the control of the human cytomegalovirus immediate early promoter. A second plasmid, pCMV3gH(792) encodes gH-1(792) which is a truncated form of the wild type protein terminating at amino acid 792 and was constructed by insertion of an SpeI linker containing termination codons within the gH coding region as described by Roberts et al. (1991, Virology 184:609).

Plasmids Expressing gL

The UL1 open reading frame which encodes gL (McGeoch et al., 1988, J. Virol. 62:1486) was amplified from viral DNA using the polymerase chain reaction (PCR). The following synthetic oligonucleotide primers containing the underlined XbaI restriction enzyme sites were designed to facilitate cloning: 5'-TGC<u>TCTAGA</u>GCGCTATGGGGA TTTTGGGT-3' (upstream primer) and 5'-TGC<u>TCTAGA</u>GGTTTCCGTCGAGGCATCGT-3' (downsteam primer) [SEQ. ID. NOS; 3 and 4, respectively]. To prepare the template for amplification, approximately $10^5$ HSV-1 virions were lysed by heating to 95° C. for 10 minutes. The lysate was added to a 100 µl PCR reaction mixture containing 2.5 units of TaqI DNA polymerase (Perkin Elmer, Cetus), 10 mM Tris-HCl (pH 8.3), 50 mM KCl, 1.5 mM $MgCl_2$, 0.001% gelatin (wt/vol), the four deoxyribonucleotides each at a concentration of 200 µM, and 1.0 µM of each of the primers. The PCR mixture was subjected to 35 cycles of amplification (94° C. for 1 minute, 55° C. for 1 minute, and 72° C. for 1.5 minutes). The product, a 718 bp fragment was digested with XbaI in order to generate cohesive termini and was then gel purified and ligated into the XbaI sites of both pCMV3 (Andersson et al., 1989, J. Biol. Chem. 264:8222) and pMMTV (Friedman et al., 1989, Mol. Cell. Biol. 9:2303) generating the plasmids pCMV3gL-1 and pMMTVgL-1, respectively. Transcription of the gL gene is thus under the control of the CMV immediate early promoter in pCMV3gL-1 and under the control of the inducible dexamethasone mouse mammary tumor virus promoter in pMMTVgL-1.

Transfection of Cells

Transient transfections were performed using calcium phosphate (Graham and van der Eb, 1973, Virology 52:456). In co-transfection assays, 4 µg/well of plasmid was used; for single plasmid transfections, 8 µg/well was used. At 42 hours post-transfection, cell supernatants were collected and assayed by immunoprecipitation and/or cells were harvested for immunofluorescence studies.

Immunoprecipitation and Gel Electrophoresis of Proteins

At 18 hours post-transfection, L cells transfected with plasmid DNA as described above were washed twice in Dulbecco's modified Eagle medium lacking cysteine (DMEM/cys-; Gibco BRL). The cells were incubated in DMEM/cys-supplemented with 200 µCi per well of $^{35}$S-cysteine and 10% FCS for 24 hours. Cell supernatants were collected, centrifuged to remove any non-adherent cells and concentrated 10-fold by centrifugation at 5520×g for 1 hour in Centricon-10 concentrator tubes (Amicon, Inc.). Concentrated supernatants were treated with 1 mM each of Nα-p-tosyl-L-lysine chloromethyl ketone (TLCK) and N-tosyl-L-phenylalanine chloromethyl ketone (TPCK) and were stored at −20° C. For immunoprecipitation, supernatants were thawed and mixed with a buffer containing 10 mM Tris-HCl, pH 8.0, 100 mM NaCl, 1 mM EDTA. 0.5% Noniodet P-40 (wt/vol), and 0.25% gelatin (wt/vol). Supernatants were incubated with 3 µl of either R83 or anti-gL serum and PANSORB H4 *Staphylococcus aureus* cells (CalBiochem). Following precipitation, immunoprecipitates were washed three times in high salt buffer (10 mM phosphate buffer, pH 7.2, containing 0.65 M NaCl, 1 mM EDTA, 1% Triton X-100) and once in low salt buffer (10 mM phosphate buffer, pH 7.2, containing 0.15 M NaCl, 1 mM EDTA, 1% Triton X-100). The immunoprecipitates were then solubilized in dissolution buffer (100 Tris HCl, pH 6.8, 4% SDS, 0.2% bromophenol blue, 20% glycerol and 10% β-mercaptoethanol), and the proteins were resolved by SDS-PAGE under denaturing conditions as described (Cohen et al., 1986, J. Virol. 60:157). Proteins in the gel were fixed, in a mixture of glacial acetic acid and methanol, the gel was impregnated with Autofluor (National Diagnostics) and was exposed to X-ray film at −70° C.

Enzymatic Treatment of Cytoplasmic Extracts and Immunoprecipitates

Cytoplasmic extracts were prepared from infected or transfected cells as described (Cohen et al., 1986, J. Virol. 60:157). Extracts were treated with 5 mU of endo-β-N-acetylglucosaminidase (endo H; Boehringer Mannheim Biochemicals) or 250 mU of endoglycosidase F/N-glycosidase F (endo F; Boehringer Mannheim Biochemicals) for 2 hours at 37° C. Immunoprecipitates were eluted from PANSORBIN cells by boiling in buffer containing 0.1 M sodium phosphate (pH 7.5), 0.5% β-mercaptoethanol and 0.1% SDS, and were diluted 2-fold in 0.1 M sodium phosphate buffer containing 1% octyl glucoside, 150 µM phenanthroline and 10 mM EDTA. Samples were then treated for 2 hours at 37° C. with 5 mU of endo H or 250 mU of endo F.

Western Blot Analysis

Following enzymatic treatment of cytoplasmic extracts, proteins were resolved by SDS-PAGE under denaturing conditions and transferred to a nylon membrane which was incubated in the presence of R82. Bound antibody was detected using goat anti-rabbit horseradish peroxidase conjugate (Boehringer Mannheim Biochemicals) and a chemiluminescent substrate solution (New England Nuclear). The membrane was exposed at room temperature to Kodak X ray film.

Immunofluorescence

To examine expression of gH and gL on the cell surface, cells transfected with plasmids expressing either protein were suspended in phosphate-buffered saline (PBS) containing 0.005 M EDTA, washed by centrifugation and resuspended in PBS containing 1% bovine serum albumin (BSA). The cells were incubated at 4° C. for 30 minutes in the presence of gH MAb alone, anti-gL-1 serum alone, or in the presence of both antibodies (for double label immunofluorescence studies). The cells were washed and further incubated in the presence of goat anti-mouse IgG F(ab')$_2$ fluorescein-labeled conjugate (to detect gH) and/or goat anti-rabbit IgG F(ab')$_2$ fluorescein-labeled or rhodamine-labeled conjugate (to detect gL). Cells so stained were visualized using a Leitz epifluorescence microscope. For double-label fluorescence studies, the same microscopic fields were viewed under fluorescein and rhodamine filters.

Additional immunofluorescence studies were performed on acetone fixed cells. Transfected cells suspended in PBS containing 1% BSA were allowed to adhere to glass microscope slides and were fixed in acetone prior to incubation in the presence of antibody and conjugate as described above.

The results of these experiments are now described.

Requirement of gL for Normal Processing of gH in Transfected Cells

Normal processing of gH requires addition of N-linked carbohydrates to the nascent molecule (Buckmaster et al., 1984, Virology 139:408). However, in the absence of other HSV-1 glycoproteins, processing of gH is incomplete. In order to establish a definitive role for gL in processing of gH, gH produced in the presence or absence of gL was analyzed for sensitivity to endo H or endo F. Treatment of incompletely processed glycoproteins with either enzyme results in cleavage of the carbohydrate moiety and a subsequent reduction in the molecular weight of the glycoprotein compared with the completely processed glycoprotein. Glycoproteins which contain complex, fully processed carbohydrate moieties are resistant to cleavage by endo H, but remain sensitive to endo F. Cytoplasmic extracts were prepared from cells which were either infected with HSV-1 or were cotransfected with pCMV3gH-1 and pCMV3gL-1, or simply transfected with pCMV3gH-1 alone, which extracts were either subsequently untreated or were incubated in the presence of endo H and endo F. It is evident from the data presented in FIG. 1 that gH exhibits sensitivity to both endo H and endo F when expressed in the absence of gL. In contrast, when gL is present either during infection or during cotransfection, the molecular weight of gH following endo H treatment is essentially unchanged indicating that gL is required for complete processing of gH in transfected cells.

Expression of gL is Required for Correct Folding of gH

Figure 2A:
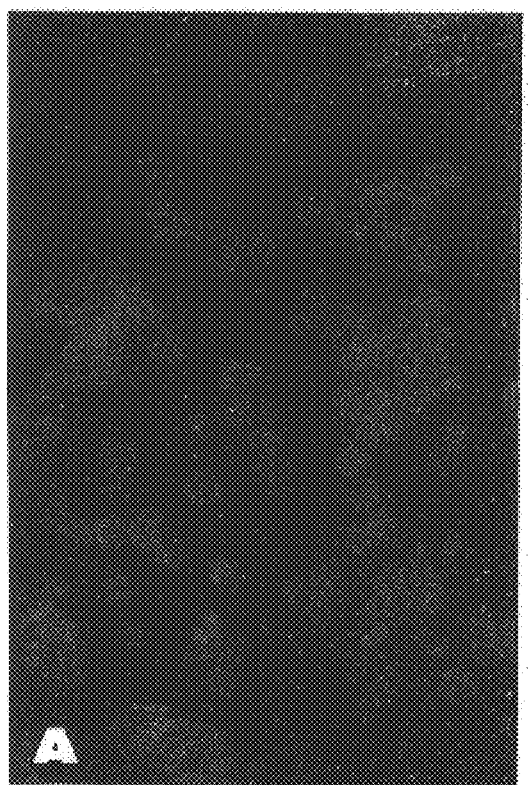
FIGS. 2A and 2B are photomicrographs depicting analysis of folding of gH. L cells transfected with pCMV3gH-1 (FIG. 2A) or cotransfected with pCMV3gH-1 and pCMV3gL-1 (FIG. 2B) were processed for immunofluorescence and were incubated in the presence of the gH monoclonal antibody (MAb) 53S (American Type Culture Collection), which antibody reacts with correctly folded gH but does not react with incorrectly folded gH.
Figure 2B:
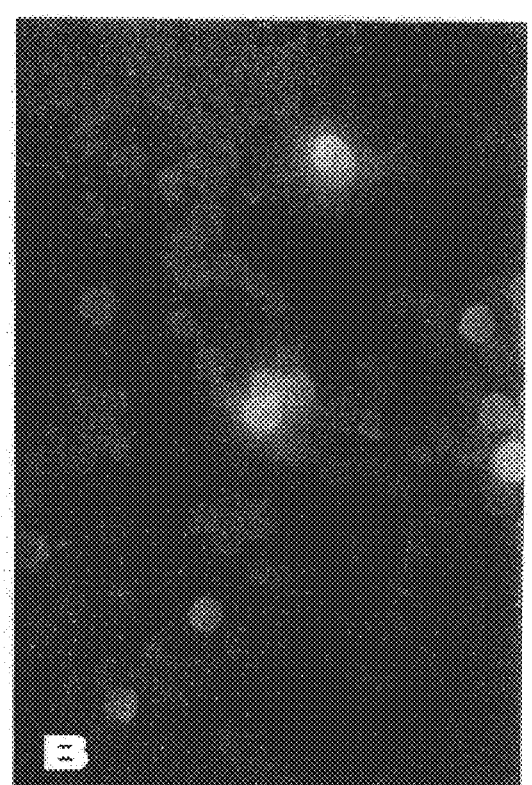

To determine whether gH is folded correctly in gL-negative cells, reactivity of gH with the conformation-dependent gH-MAb, 53S, was examined by immunofluorescence. Extracts of L cells transfected with pCMV3gH-1 did not react with 53S (FIG. 2A), whereas extracts of cells transfected with both pCMV3gH-1 and pCMV3gL-1 exhibited strong reactivity (FIG. 2B). Similar results were observed using LP11, a gH MAb which reacts with a distinct conformation phenotype of gH (Gompels et al., 1991, J. Virol. 65:2393). These results indicate that, in transfected cells, folding of gH is normal in the presence of gL but is abnormal in the absence of gL.

Expression of gL is Required for Intracellular Transport and Cell Surface Expression of gH in Transfected Cells To examine the effect of expression of gL on intracellular transport and cell surface expression of gH, L cells were transfected with pCMV3gH-1 either alone or in combination with pCMV3gL-1. The intracellular localization of gH in cells so transfected was assessed by immunofluorescence using the MAb 37S, a MAb which binds to gH irrespective of its structural conformation (Roberts et al., 1991, Virology 184:609). In the absence of gL, the intracellular distribution of gH was cytoplasmic and included some perinuclear localization suggesting retention of this glycoprotein in the endoplasmic reticulum (FIG. 3A). However, in the presence of gL, gH was distributed throughout the cell in a uniform manner with some localization at the cell perimeter suggesting cell surface expression (FIG. 3B). To examine cells surface expression in more detail, these studies were repeated using unfixed cells. In this instance, gL was expressed from the dexamethasone-inducible plasmid pMMTVgL-1. Thus, cells were cotransfected with pCMV3gH-1 and pMMTVgL-1 and were subsequently incubated either in the presence or absence of dexamethasone. Cells so transfected were treated with the gH MAb 37S, and with anti-gL serum, and were then stained with fluorescein-labeled conjugate (to detect gH) and rhodamine-labeled conjugate (to detect gL). In cells incubated in the presence of dexamethasone, both gH and gL co-localized to the cell surface (FIG. 4A and FIG. 4B). This was also true when cells were cotransfected with pCMV3gH-1 and pCMV3gL-1 (FIG. 4E and FIG. 4F). However, in the absence of dexamethasone, neither glycoprotein was found at the cell surface. Thus, gL is required for intracellular processing of gH.

Membrane Association of gL Results from its Association with gH

The predicted amino acid sequence of gL suggests that it is a secreted rather than a membrane associated glycoprotein (McGeoch et al., 1988, J. Gen. Virol. 69:1531). To investigate whether gL is capable of independent association with the cell membrane (i.e., in the absence of membrane association by gH), gL was co-expressed with a mutant of gH, which mutant lacks the membrane spanning domain of the glycoprotein (gH792). In cells transfected with a plasmid encoding gL, or with a plasmid encoding gL and the truncated form of gH, gL was not detected on the cell surface (FIG. 5B and FIG. 5D); however, in cells transfected with plasmids encoding gL and full length wild type gH, gL was detected on the cell surface (FIG. 5F). That gL was actually expressed in each of these sets of transfected cells was confirmed by immunofluorescence of permeabilized cells (FIG. 5A, FIG. 5C and FIG. 5E). These data demonstrate that cell surface expression of gL is dependent upon expression of wild type gH.

Secretion of gL

To examine secretion of gL from transfected cells, cells were transfected with the following combinations of plasmids: pCMV3gL-1 alone; pCMV3gL-1 plus pCMV3gH (792); or, pCMV3gL-1 plus pCMV3gH-1. In each instance, proteins synthesized by these cells were labeled with $^{35}$-cysteine, they were extracted from the cell supernatants and were analyzed by immunoprecipitation using anti-gL serum. A 30 kDa protein (gL) was identified in supernatants from cells transfected with pCMV3gL-1 alone and in cells transfected with pCNV3gL-1 plus pCMV3gH(792). This protein was not identified in supernatants from cells cotransfected with pCMV3gL-1 and pCMV3gH-1 (FIG. 6). A protein of 105 kDa in size was also immunoprecipitated by anti-gL serum and by R83 (anti-gH MAb) in cells cotransfected pCMV3gL-1 plus pCMV3gH(792) suggesting that both gL and the truncated form of gH are secreted from these cells as a complex (FIGS. 6 and 7). Neither the 30 nor the 105 kDa proteins were evident in supernatants from cells transfected with pCMV3gH(792) alone. Thus, these experiments demonstrate that gL and gH are capable of forming a complex at the cell surface and that gL does not independently associate with the cell membrane, rather, its association with this membrane is dependent upon the presence of the membrane anchor portion of gH. The finding that gL is secreted from cells independent of gH was unexpected since previous studies suggested that processing of gL required the presence of gH (Hutchinson et al., 1992, J. Virol. 66:2240).

Figure 8:
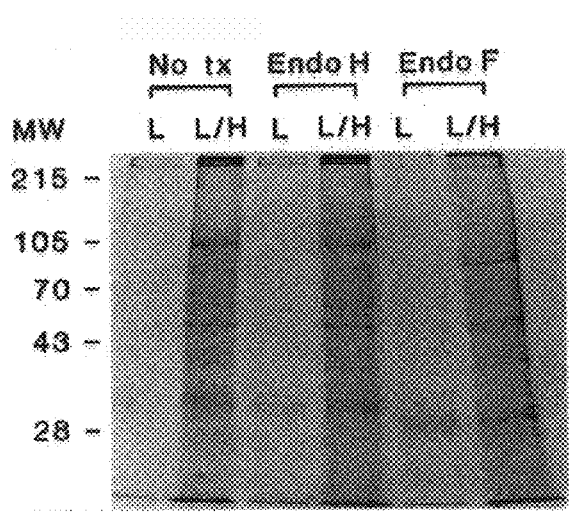
FIG. 8 is a photograph of a gel depicting analysis of carbohydrate processing of gL secreted by cells. L cells were transfected with pCMV3gL-1 alone or with pCMV3gL-1 plus pCMV3gH(792). Transfected cells were incubated in the presence of $^{35}$S-labeled cysteine. Supernatants were collected from cells so incubated, which supernatants were concentrated and immunoprecipitated with anti-gL serum. Immunoprecipitated proteins were treated with endo H, endo F, or were untreated and the products were resolved by SDS-PAGE. Abbreviations: L, pCMV3gL-1; H, pCMVgH (792); no tx, no treatment.

Confirmation that gH is not Required for Processing of the Carbohydrate Moiety of gL To further investigate the role of gH in processing of gL, cells were transfected with either pCMV3gL-1 alone or were cotransfected with pCMV3gL-1 and pCMV3gH(792). Supernatants were collected from cells so transfected and any gL present therein was examined for sensitivity to either endo H or endo F. The same pattern of enzyme sensitivity was evident irrespective of the presence or absence of gH (FIG. 8). Therefore, gH is not required for either the addition or processing of N-linked carbohydrates on gL expressed in transfected cells.

The region of gH Required for Complex Formation with gL

Figure 9:
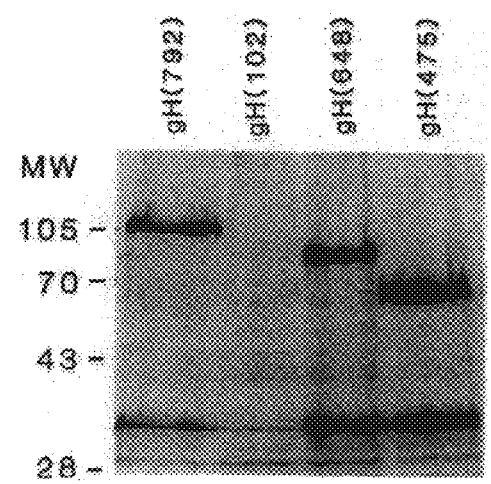
FIG. 9 is a photograph of a gel depicting analysis of complex formation between gL and various truncated mutant forms of gH. L cells were cotransfected with pCMV3gL-1 and with one of the following plasmids encoding truncated forms of gH as indicated at the top of the gel: pCMV3gH(792); pCMV3gH(648); pCMV3gH(475); and, pCMV3gH(102). Transfected cells were incubated in the presence of $^{35}$S-labeled cysteine. Supernatants were collected from cells so incubated, which supernatants were concentrated and immunoprecipitated with anti-gH serum. Immunoprecipitated proteins were resolved by SDS-PAGE.

As described above, coexpression of gL with the truncated form of gH [gH(792)] results in a complex comprising the two proteins, which complex is secreted from cells. To determine which domains of gH are required for complex formation, additional mutants of gH, expressing further truncated forms of this glycoprotein, were tested in the transfection assay described above. The mutants tested were as follows: gH(648), gH(475), and gH(102), each of which expresses a protein of 648, 475 and 102 amino acids in length. The plasmids encoding these mutated forms of gH are designated pSR124 (648), pSR123 (475) and pSR125 (102). Each plasmid encodes the truncated form of gH under the control of the Rous sarcoma virus promoter (Roberts et al., 1991, Virology 184:609). Cells were cotransfected with pCMV3gL-1 and with one of the mutant plasmids described above and were incubated in medium containing $^{35}$S-cysteine. At 18 hours post-transfection, cell supernatants were harvested and the proteins contained therein were immunoprecipitated with anti-gH serum. as described above. Immunoprecipitates were resolved by SDS PAGE and the results are shown in FIG. 9. Mutant forms of gH which terminate at amino acid residues 792, 648 and 475 were secreted from cotransfected cells in a complex with gL. However, when a mutant encoding only 102 amino acid residues of gH was used, a gH-gL complex was not detected in cell supernatants. Additional experiments have been conducted in a similar manner to that described above and it is now believed that a region of gH comprising amino acids 1–324 and a region comprising amino acids 1–275 are capable of forming a complex with gL. Thus, the region of gH required for interaction with gL resides in the amino-terminal portion of the molecule between residues 1–275. As noted above, the membrane anchor region of gH resides in the carboxyl terminus of the molecule between amino acid residue 792 and the last amino acid residue at the carboxyl terminus.

Construction of a Stable gH-gL Expressing Cell Line

For the purposes of vaccine production, generation of a gH-gL complex in the cell lines described below has significant advantages over other methods of production of this complex which methods may involve for example, extraction of a gH-gL complex from infected cells. In the latter case, since wild type gH comprises a hydrophobic membrane anchor region, it is necessary to use detergents during extraction to remove the membrane portion. Such treatment may in fact alter the conformation of the complex and thereby alter its immunogenic properties. By using the cell lines described below, a secreted form of gH is produced as a complex with gL and thus, further extraction and purification prior to use as a vaccine is minimized. In addition, the use of mammalian cells is advantageous in that both insect and lower eukaryotic cells each process carbohydrates somewhat differently than do mammalian cells. Thus, the use of mammalian cells ensures correct processing of the components of the complex and thereby ensuring preservation of the immunologically protective epitopes within the complex.

Figure 10:
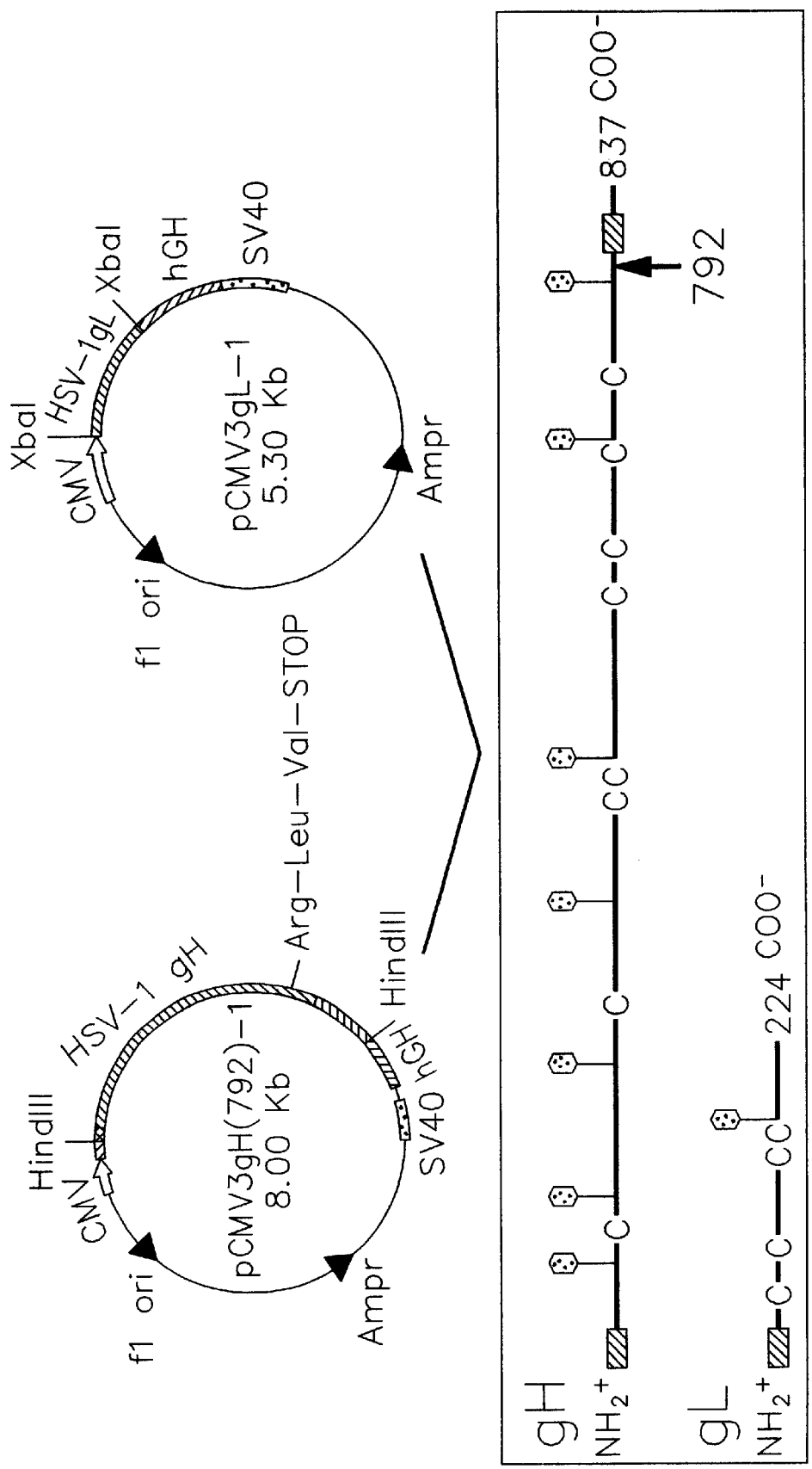
FIG. 10 is a diagram of the plasmids used to construct the HL-7 cell line and diagrammatic representations of gHt and gL. HL-7 cells were obtained by co-transfecting mouse L cells with pCMV3gH(792)-1, pCMV3gL-1 and pX343, which confers resistance to hygromycin B (Blochlinger et al., 1984, Molecular & Cellular Biology. 4:2929–2931). HL-7 was one of four separate clones which expressed and secreted gHt-gL as a complex. The stick diagrams illustrate major structural features of full length gH-1 and gL-1. An arrow indicates the location of the truncation of gH at amino acid 792. Balloons indicate positions of predicted N-linked oligosaccharides and C indicates positions of cysteine residues. The predicted signal peptide and transmembrane anchor regions are indicated with shaded boxes.

A diagram of the plasmids used to generate a gHt-gL expressing cell line, and a map of gH and gL is provided in FIG. 10.

Cell lines which constitutively express and secrete gH-gL as a complex were constructed as follows. L cells were cotransfected with pCMVgH(792) and pCMVgL-1 and with the plasmid pX343 which encodes a gene conferring resistance of cells to hygromycin B (Blochlinger et al., 1984, Mol. Cell. Biol. 4:2929). Cells so transfected were incubated in the presence of hygromycin B (200 μg/ml). Twenty four clones of hygromycin B resistant cells were selected and supernatants therefrom were first screened for production of gH by Western blot analysis. Of these, two clones were further tested for production of both gH and gL by immunoprecipitation. Both of these clones expressed and secreted the gH-gL complex. One of these clones, designated HL-7, produced large amounts of the complex and was therefore selected for additional studies.

Figure 11:
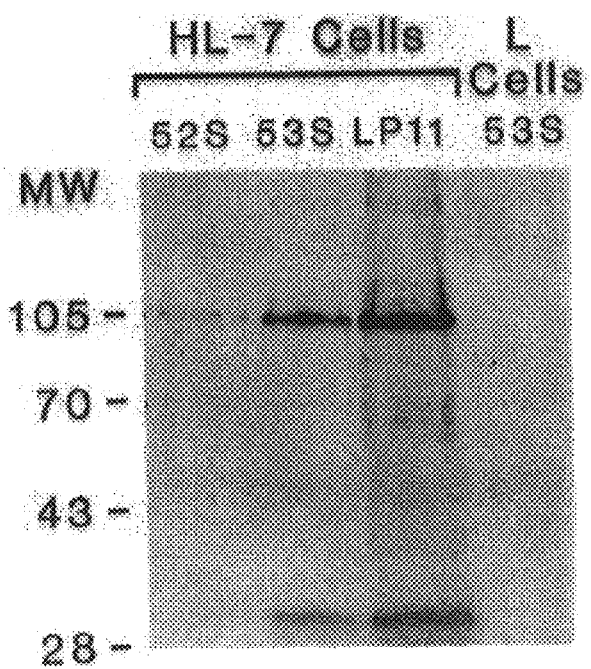
FIG. 11 is a photograph of a gel depicting immunoprecipitation of gH-gL complex secreted by HL-7 cells. Proteins produced by HL-7 cells were labeled with $^{35}$S-cysteine, cell supernatants were obtained and were immunoprecipitated with gH MAbs 52S, 53S and LP11 as indicated at the top of the figure. As a control, proteins produced by L cells, also labeled with $^{35}$S-cysteine, were immunoprecipitated with 53S. Immunoprecipitated proteins were resolved by -SDS-PAGE.

The gH-gL complex secreted by HL-7 cells was found to be immunoprecipitable by gH MAbs 52S, 53S, and LP11 (FIG. 11). Since these MAbs are dependent upon correct folding of gH in that they react with distinct structural epitopes on the molecule, the gH-gL complex secreted by HL-7 cells appears to have a structure similar to that of the wild type complex.

Identification of a Putative Membrane Fusion Region of gH

A computer-based analysis of the amino acid sequence of gH was performed and revealed a region of the protein predicted to form an amphophilic a-helix extending from approximately amino acid residues 280–310, which helix is indicative of a membrane fusion region in influenza virus (White, 1992, Science 258:917). A gH expression plasmid (derived from pCMV3gH-1) was constructed wherein amino acid residues 275–324 were deleted (i.e., the deleted amino acid residues encompass the putative membrane fusion region) and a linker encoding 5 amino acids was inserted at the site of the deletion to re-establish the correct reading frame. The resulting gH mutant, pCMVgHΔ (275–324), encodes a protein which folds correctly and is transported to the cell surface when expressed in cells also expressing wild type gL. Furthermore, this deleted gH retains the ability to form a complex with gL as assessed in the co-immunoprecipitation assay described above. The ability of the deleted gH to rescue a gH negative virus was determined in a complementation assay as follows. L cells were transiently transfected with pCMVgH-1 or pCMVgHΔ (275–324), or were mock transfected. At 18 hours post-transfection, cells were infected with a gH negative mutant virus and incubation was continued for an additional 24 hours. The amount of virus produced was then assessed by plaque assay. Cells transfected with pCMVgH-1 produced $2.5\times10^5$ infectious virus per ml while mock transfected cells produced less than $1.5\times10^2$ virus per ml. Cells which were transfected with pCMVgHΔ(275–324) also produced negligible amounts of infectious virus i.e., less than $1.5\times10^2$ virus per ml, indicating that this plasmid was incapable of rescuing the gH negative phenotype exhibited by the gH negative virus. Thus, deletion of gH in the region of amino acid residues 275–324 renders the protein non-functional.

EXAMPLE 2

The experiments which establish that gH-gL complex functions to neutralize virus infectivity and protect animals against challenge by wild type infections virus are now described. The Materials and Methods used in these experiments are presented below.

Cells and Virus

African green monkey kidney (Vero) and mouse L cells were grown in Dulbecco's Modified Eagle Medium (DMEM) supplemented with 5% fetal bovine serum (FBS) at 37° C. D14 cells (Vero derived) which express HSV-1 ICP6 (Goldstein et al., 1988, J. Virol. 62:2970–2977) were grown in DMEM with 5% FBS and G418 (25 μg/ml) at 37° C. HL-7 cells which express gHt-gL were grown in DMEM supplemented with 10% FBS and hygromycin B (50 μg/ml). For protein production, hygromycin B was eliminated from the medium. HSV-1(hrR3) (Goldstein, supra) was propagated on D14 cells and titered on Vero cells. The propagation of HSV-1 (NS) and HSV-2 (333) virus stocks have been described (Eisenberg et al, 1987, Microb. Pathog. 3:423–435).

Antibodies

The monoclonal antibody (MAb) secreting cell lines, 52S and 53S (recognizing gH-1) (Showalter et al., 1981, Infect. Immun. 34:684–692) were obtained from the American Type Culture Collection. Anti-gH MAb 37S is described in Showalter et al., supra). Anti-gH MAb LP11 is described in Buckmaster et al. (1984, Virology 139:408–413). MAb 8H4, which recognizes a linear epitope on gL is described herein and in Dubin et al. (1995, J. Virol. 69:4564–4568); Rabbit antibody αUL–2, which was prepared against a peptide sequence of gL is described in Hutchinson et al. (1992, J. Virol. 66:2240–2250). Rabbit antibody R83 (against gH) is described herein and in Roberts et al. (1991, Virology 184:609–624). Polyclonal antibodies R137, R138, R139 and R140 were prepared against purified gHt-gL as described herein.

Purification of gHt-gL Complex from the Supernatant of HL-7 Cells

The construction of the HL-7 cell line has been described herein. To obtain gHt-gL complex from HL-7 cells, the cells were grown in roller bottles. The supernatant was obtained after 3 days and replaced with fresh medium. Two "harvests" of supernatant were obtained from each roller bottle.

The secreted gHt-gL complex was purified by chromatography on an immunoaffinity column of 53S, a gH-1 specific MAb, by a modification of a previously method used to purify gH from extracts of HSV-1 infected cells (Roberts et al, 1991, Virology 184:609–624). In the present experiment, the clarified medium was passed over the column, and the bound protein was eluted with a low pH buffer consisting of 50 mM glycine, 0.5 M NaCl, pH 2.5. The eluate was neutralized with 1 M Tris-base (pH 9.0) and was concentrated. Protein was quantitated by using the BCA kit (Pierce). Approximately 400 µg of gHt-gL complex was obtained per liter of HL-7 cell supernatant (approximately $10^{-4}$ ng/cell).

Figure 12:
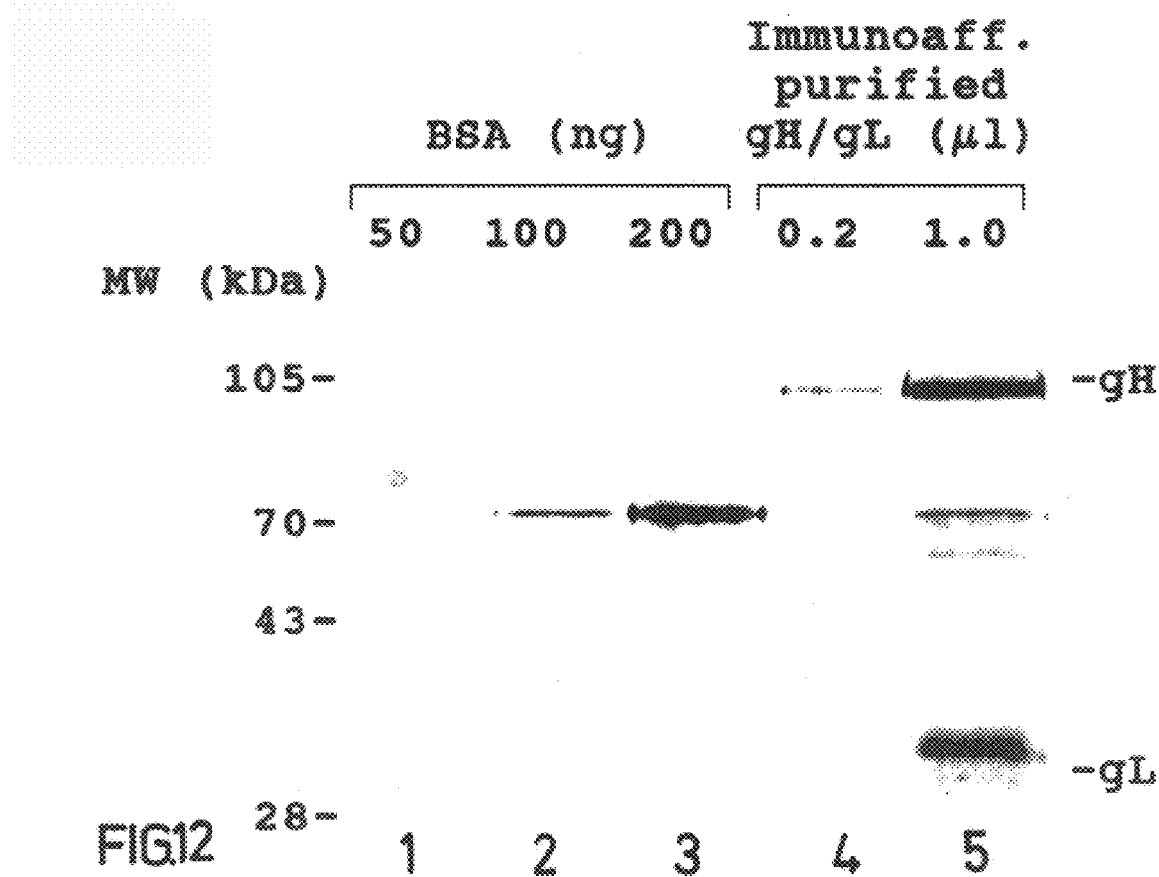
FIG. 12 is a photograph of an SDS-PAGE depicting immunoaffinity purification of gHt-gL complex secreted from HL-7 cells. Lanes 1–3, 50 nanograms, 100 nanograms and 200 nanograms of bovine serum albumin, respectively; lanes 4 and 5, 0.2 µl and 1.0 µl of pooled and concentrated 53S immunoaffinity column purified gHt-gL complex, respectively.

To quantitate the amount of complex obtained in the concentrated samples, the intensity of staining of the gH and gL bands on SDS-PAGE was compared with known quantities of protein standard (bovine serum albumin). These data are presented in FIG. 12. It is estimated that each sample contained approximately 0.5 µg/µl of gH-gL complex. It is possible to purify 0.5 mg of gH-gL complex from approximately 1 liter of HL-7 supernatant using the procedures described herein. Further, densitometric analysis of the silver stained gel indicates that gH and gL are present in the complex at a purity of approximately 90%. In addition, approximately 50% of the gH-gL complex secreted from HL-7 cells possess a conformation which is indistinguishable from that of the native molecule as assessed by binding to the 53S MAb.

Purification of HSV-1

Virus was purified as described in Handler et al. (1996, J. Virol. 70:6067–6075). Briefly, roller bottles (850 cm$^2$) of D14 cells were infected with hrR3 at an MOI of 0.1. The growth medium was collected at 24 h post infection and extracellular virus was pelleted by centrifugation at 100,000×g through a 5% sucrose-PBS cushion. Virus was further purified by first resuspending the pellet in PBS, followed by centrifugation at 30,000×g for 5 hours through a 10–30–60% sucrose-PBS step gradient. The virus band located at the 30–60% sucrose interface was collected, titered and stored at −80° C.

Soluble HSV Glycoproteins and Infected Cell Extracts

Soluble gD1 (306t) was produced in baculovirus infected Sf9 cells and was purified as described (Sisk et al., 1994, J. Virol. 68:766–775). Cytoplasmic extracts of HSV-1 (NS) (Friedrnan et al., 1984, Nature (London) 309:633–635) or HSV-2 (333) infected cells were prepared as described (Eisenberg et al., 1987, Microb. Pathog. 3:423–435; Eisenberg et al., 1982, J. Virol. 41:1099–1104). Full length gD-1 was purified from cytoplasmic extracts of HSV-1 infected cells (Eisenberg et al., 1987, Microb. Pathog. 3:423–435). Soluble gC-1(457t) was produced from baculovirus infected insect cells and was purified as described (Ta1-Singer et al., 1995, J. Virol. 69:4471–4483).

SDS-PAGE and Western Blot Analysis

SDS-PAGE under denaturing or "native" conditions was performed as described in Cohen et al. (1986, J. Virol. 60:157–166), using Tris-Glycine 10% or 4–12% gradient precast gels (Novex Experimental Technology). Silver staining was performed using a silver staining kit (Pharmacia Biotech). For Western-blot analysis, proteins were transferred to nitro cellulose, probed with anti-serum R83 for gH or MAb 8H4 for gL. Goat anti-rabbit (in the case of R83) or anti-mouse (in the case of 8H4) IgG-Peroxidase (Boehringer) was then added as secondary antibody and bands were visualized on X-ray film after the addition of ECL chemiluminescent substrate (Amersham). To strip the blot, 50 mM glycine, 0.5 M NaCl, pH 2.5 was added and the blot was incubated at room temperature for 15 minute. The blot was then washed with PBS-0.2% Tween and was reprobed.

Antigenic Analysis of gHt-gL by ELISA

Various concentrations of gHt-gL were coated onto ELISA plates and incubated overnight at 4° C. The plates were blocked with PBS containing 1% bovine serum albumin ( MSA) and 1% ovalbumin (OVA). MAbs LP11, 53S and 37S were each diluted in PBS containing 0.05% BSA and 0.05% OVA and were then added to the ELISA plate to detect the presence of gH. After 1 hour at room temperature, the plate was washed three times with PBS-0.5% Tween 20. Goat-anti-mouse-IgG-horseradish peroxidase conjugate (Boehringer) was added and the plate was incubated at room temperature for 30 minutes. After a rinse with citrate buffer (20 mM citrate acid, pH 4.5), ABTS substrate (2,2'-azino-di-3-ethylbenzthiozoline-6-sulfonic acid, Moss, Inc.) was added and absorbance was read at 405 nm using a microtiter plate reader (Biotek).

HSV-1 entry Assay

Vero cells were seeded onto a 96 well plate and grown to confluence. The plate was cooled at 4° C. for 10 minutes, and viral glycoproteins which had been serially diluted in 5% FBS DMEM (with 0.03 M HEPES) were added. The medium was removed and replaced with 50 µl of a single purified virion glycoprotein and incubated at 4° C. for 90 minutes. Purified HSV-1(hrR3) in 5% FBS DMEM ($2\times10^4$ PFU/ml) was added to each well (the MOI was 0.5 PFU/cell) and the wells were incubated at 4° C. for 90 minutes to allow virus to attach to the cells. The cells were then incubated for 5 hours at 37° C. and were lysed with 1% NP40 in DMEM. 50 µl of lysate obtained from each well was transferred to an ELISA plate, mixed with 50 µl CPRG (4.8 mg/ml) (Chlorophenolred-β-D-galactopyranoside, Boehringer) and β-galactosidase activity was measured by measuring the absorbance at 570 nm every 2 minutes for a total of 25 measurements using an ELISA plate reader (Bio-Tek). The slope of the line was used to calculate the amount of β-galactosidase activity as mOD/min.

Immunization of Rabbits with gHt-gL

New Zealand rabbits were immunized with gHt-gL mixed with one of two adjuvants (Set I and Set II) as follows. Rabbits in Set I were immunized with gHt-gL (150 µg total) mixed with Freund's adjuvant. The first dose was in Freund's Complete adjuvant (Sigma) and subsequent injections were given in Freund's incomplete adjuvant. Rabbits in Set II were immunized with gHt-gL mixed with an equal volume of Alum adjuvant (Pierce Chemical Co.).

Virus Neutralization Assay

Rabbit or mouse sera were treated at 56° C. for 30 minutes to inactivate complement. Serial two fold dilutions of serum were prepared in DMEM containing 5% FBS. The serum was then mixed with an equal volume of HSV-1 or HSV-2 adjusted to yield 100 plaques per well in the absence of neutralizing antibody. The virus cell mixture was incubated for 1 hour at 37° C., and was then overlaid with medium and was incubated at 37° C. for 24 hours. The medium was removed, the cells were fixed in a 2:1 mixture of methanol and acetone and were dried. Plaques were visualized using a cocktail of polyclonal antibodies to gD, gB and gC, by "black plaque assay" (Highlander et al., 1987, J. Virol. 61:3356–3364; Tal-Singer et al., 1995, J. Virol. 69:4471–4483) using horseradish peroxidase conjugated protein A, followed by addition of the substrate 4-chloro-1-naphthol. The neutralization titer was expressed as the dilution of serum that reduced the number of plaques by 50%.

Two assays were used to measure serum blocking (neutralization) of virus entry. In the first (antibody+virus method), each antiserum was mixed with $4 \times 10^5$ PFU/ml hrR3 in DMEM containing 5% FBS, and 0.03 M HEPES, and the serum-virus mixture was incubated at 37° C. for 90 minutes, cooled to 4° C. and added to Vero cells in 96 well plates in a volume of 100 μl/well. Plates were rocked at 4° C. for 90 minutes, then shifted to 37° C. for 5 hours. Cells were lysed and β-galactosidase activity was measured in the cytoplasmic extract. In the second assay (antibody after virus method), $4 \times 10^5$ PFU/ml of hrR3 in DMEM containing 5% FBS and 0.03 M HEPES was added to Vero cells at 4° C. for 90 minutes. The virus was removed and replaced by antiserum diluted in DMEM containing 5% FBS. Plates were rocked at 4° C. for 90 minutes, then shifted to 37° C. for 5 hours. Cells were lysed and β-galactosidase activity was measured.

Murine Flank(Zosteriform) Model of HSV Challenge

A zosteriform model of HSV-1 infection (Simmons et al., 1985, J. Virol. 53:944–948; Simmons et al., 1984, J. Virol. 52:816–821) was used to test the efficacy of gHt-gL as a vaccine. Nine to ten week old Balb/c (Charles River) mice were immunized intraperitoneally with 10 μg antigen in complete Freund's adjuvant, followed by three additional 10 μg doses of antigen given in incomplete Freund's adjuvant at two week intervals. The antigens used were purified gHt-gL produced by HL-7 cells, or purified full length gD-1 purified from HSV-1 infected cells (Eisenberg et al., 1987, Microb. Pathog. 3:423–435). Sham-immunized control animals received PBS emulsified with adjuvant at the same intervals. Mice were bled and sera were obtained therefrom between the third and fourth immunizations to test for virus neutralization. Two weeks after the last immunization, the right flank of each immunized or control animal was shaved and denuded using a dipilatory cream. Twenty four hours later, $5 \times 10^5$ PFU of HSV-1 was applied to the depilated flank approximately 3 mm ventral to the spinal column and the skin was scratched with a 27 gauge needle using 20 horizontal strokes and 20 vertical strokes over an approximate area of 3×3 mm. The flank was observed daily for at least 10 days and cumulative scores for primary and secondary areas were recorded for days 3 through 8. The period of recording lesions was limited to this period due to the deaths of unprotected animals beginning at day 8. Disease at the inoculation site was scored as follows: 0 points for no disease; 0.5 for swelling without vesicles; and 1 point each for each vesicle or scab to a maximum score of 5. Swelling and lesions in locations separate from the inoculation site were considered to be secondary or zosteriform disease. Scoring of these lesions was the same as for the inoculation site except that a daily maximal score of 10 was used.

The results of these experiments are now described.

HL-7 cells secreted significant amounts of gHt-gL which was detected on western blots at the predicted sizes for gHt and gL as described herein.

Purification and Analysis of gHt-gL gHt-gL was purified from the growth medium of HL-7 cells by immunoaffinity chromatography on an anti-gH(53S) MAb column as described herein. Purification was monitored by SDS-PAGE followed by silver staining (FIG. 13A) as well as by western blot analysis (FIG. 13B, FIG. 13C). The purified complex contained two silver stained bands of 110 kDa and 35 kDa in size (FIG. 13A, lane 3), although neither of these glycoproteins was prominent in the culture supernatant or column flow through (FIG. 13A, lanes 1 and 2). Both glycoproteins were readily detected in the culture supernatant by western blot analysis (FIG. 13B, FIG. 13C, lanes 1). The absence of both gH and gL from the column flow through fraction (FIG. 13B, FIG. 13C, lanes 2) established that all of the secreted gL was associated with gH and both proteins bound to MAb 53S as a stable complex. Both proteins were eluted by low pH (FIG. 13B, FIG. 13C, lanes 3). It was estimated that the eluted complex was greater than 95% pure by silver stain (FIG. 13A, lane 3).

Figure 14B:
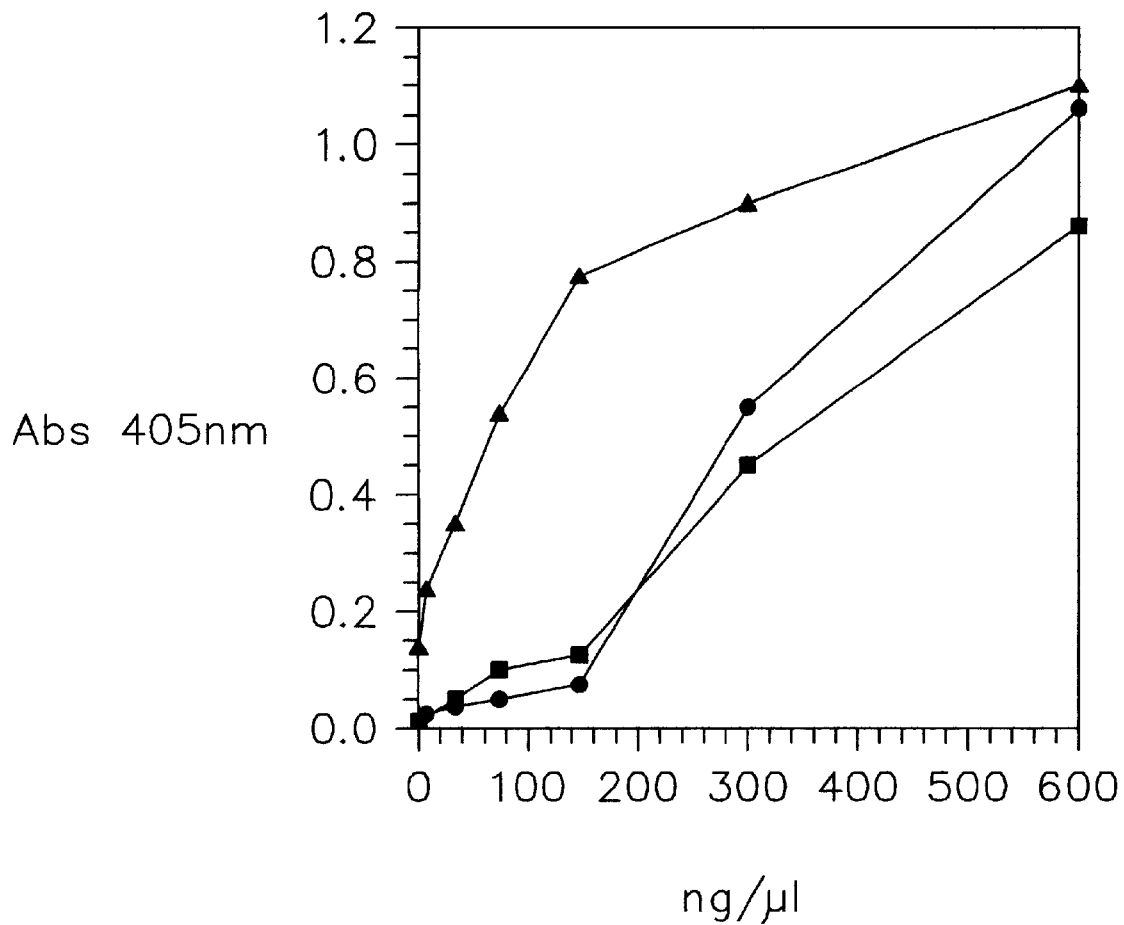

LP11 reactivity is considered to be a critical test of gH-gL conformation, since this MAb only reacts with gH when it is part of the native complex (Hutchinson et al., 1992, J. Virol. 66:2240–2250). Secondly, LP11 neutralizes virus infectivity at high titers and therefore recognizes an immunologically important epitope (Buckmaster et al., 1984, Virology. 139:408–413). Purified gHt-gL was immunoprecipitated using LP11, separated by SDS-PAGE, and analyzed by Western blotting, probing for gH (FIG. 14A, lane 1) and gL (FIG. 14A, lane 2) on individual nitrocellulose strips. Both proteins were detected establishing that the complex was reactive with LP11. Similar results were obtained using MAb 52S (Showalter et al., supra) in the initial immunoprecipitation. In a second method, ELISA was used to establish that the purified complex reacts with MAbs LP11, 53S and 37S (Showalter et al., supra). Previous studies established that MAbs 52S, 53S and LP11 recognize different conformation dependent epitopes (Forrester et al., 1991, J. Gen. Virol. 72:369–75; Fuller et al., 1989, J. Virol. 63:3435–3443; Fuller et al., 1989, J. Virol. 63:3435–3443; Roberts et al., 1991, Virology. 184:609–624) and 37S recognizes a linear epitope (Roberts et al., 1991, supra). Thus, these two experiments indicate that gHt in the complex is antigenically correct. Similar studies were not done on gL, as no conformation dependent MAbs are available. However, the complex does react by ELISA with gL MAbs which recognize linear epitopes.

gHt-gL Does not Inhibit Virus Entry

Both gH-1 and gL-1 are essential for HSV-1 penetration and cell-to-cell spread and are most likely involved in a cell fusion event (Davis-Poynter et al, 1994, J. Virol. 68:7586–7590; Desai et al., 1988, J. Gen. Virol. 69:1147–56; Forrester et al., 1992, J. Virol. 66:341–348; Novotny et al., 1996, Virology 221:1–13; Roop et al, 1993, J. Virol. 67:2285–2297). However, little is known about gH-gL function, or whether the proteins work individually or together with other glycoproteins to effect virus entry. Soluble forms of gD (gDt) are able to block HSV infection (Johnson et al., 1990, J. Virol. 64:2569–2576; Nicola et al., 1997, J. Virol. 71:2940–2946; Nicola et al., 1996, J. Virol. 70:3815–3822). This is due to the interaction of gDt with cellular receptors such as HVEM (Montgornery et al., 1996, Cell. 87:427–436; Whitbeck et al., 1997, J. Virol. 71:6083–6093), rendering these receptors unavailable for binding to gD in the virion. In contrast, soluble forms of gC-1 (gC-1t) do not block plaque formation by HSV (Tal-Singer et al., 1995, J. Virol. 69:44714483). It has recently been reported that gC-1t, gB-1t and gHt-gL do not bind directly to HVEM (Whitbeck et al., 1997, supra).

Figure 15A:
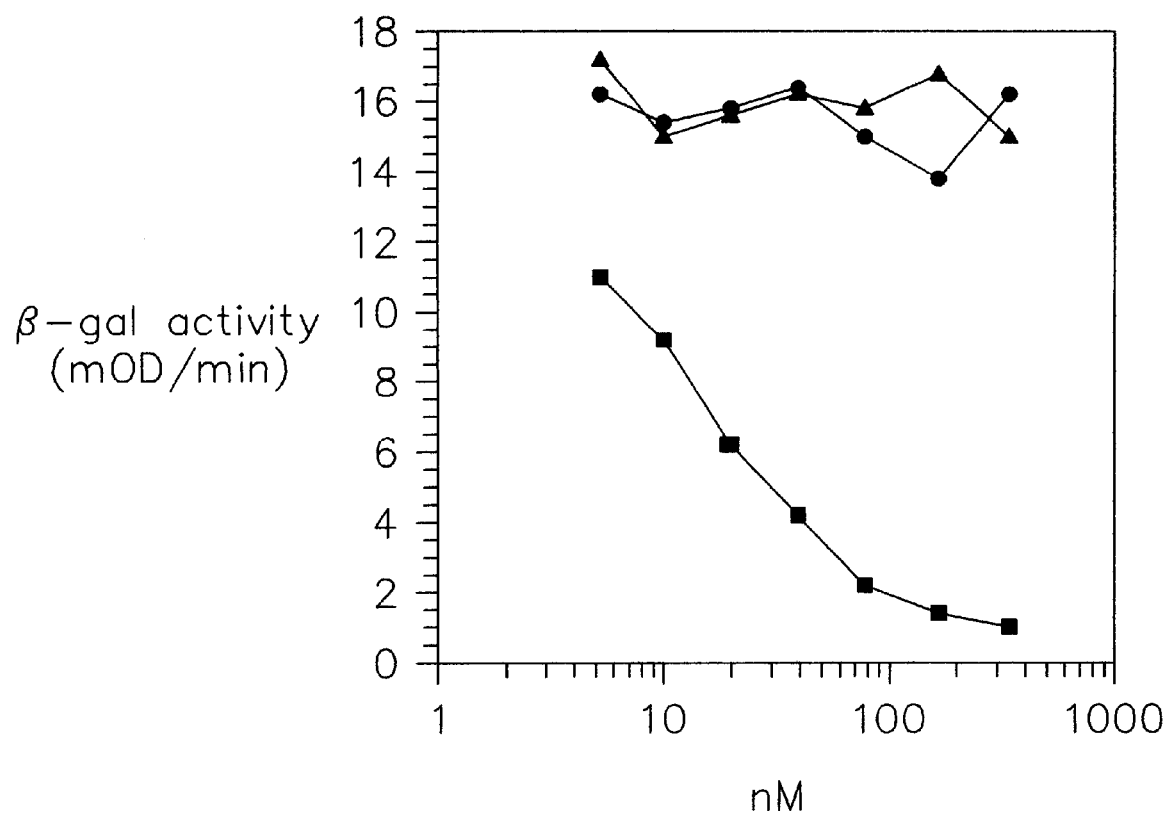
In FIG. 15A, there is shown blocking of virus entry with purified gCt, gDt or gHt-gL.

The question in the present study is whether soluble gHt-gL is able to block HSV-1 entry into cells, perhaps by binding to a different receptor than HVEM. To answer this, an entry assay employing HSV-1(hrR3) which contains the lacZ gene under the control of the ICP6 promoter was used (Goldstein et al., 1988, J. Virol. 62:2970–2977). Virus entry was measured as an increase in β-galactosidase activity at 5 hours post-infection (FIG. 15A). As expected from previous studies (Ta1-Singer et al., 1995, supra), gC-1t did not block virus entry and served as a negative control for the assay. Fifty percent inhibition of virus entry was observed at 50 nM gD-1(306t), a result similar to that obtained using a 50% inhibition of plaque formation assay (Tal-Singer et al., 1995, supra). In contrast, gHt-gL did not inhibit virus entry even at protein concentrations as high as 350 nM (50 ng/μl).

Figure 15B:
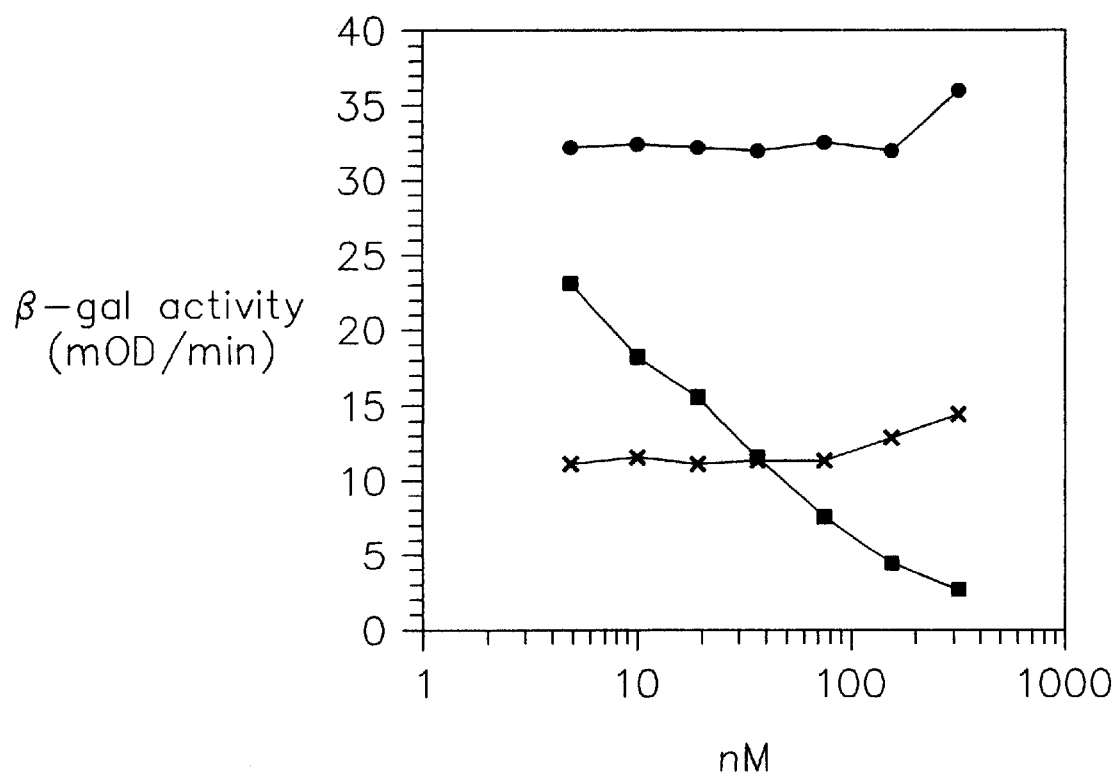
In FIG. 15B, there is shown blocking of virus entry with gDt alone, gHt-gL or a mixture of 40 nM gD (concentration which resulted in 50% inhibition of virus entry) with various concentrations of gHt-gL.

To determine whether gHt-gL enhanced the ability of soluble gD-1(306t) to block infection by enhancing its binding to HVEM or other gD receptors, the following experiment was carried out. Increasing amounts of gHt-gL were added to cells together with 40 nM gD (FIG. 15B). At this concentration, gD inhibited virus entry by 40–50%. gHt-gL did not enhance the inhibition achieved with gDt alone.

Antibodies to gHt-gL Block Virus Entry and Neutralize Virus Infectivity

The previous experiments were inconclusive as to the role played by gH-gL in virus entry. It was previously shown that anti-gH neutralizing MAbs such as LP11 are able to block HSV infection even when added after virus attachment (Fuller et al., 1989, J. Virol. 63:3435–3443). It was therefore hypothesized that if the conformation of gHt-gL is close to that of the functional form in the virus, then antibodies to the complex should be able to neutralize infection and block virus entry whether added before or after virus attachment.

To test this hypothesis, rabbits were immunized with gHt-gL using either Freund's or alum adjuvant. All four animals produced antibodies which recognized gHt and gL on western blot of a denaturing gels (FIG. 16A). On a western blot of a non-denaturing (native) gel (Cohen et al., 1986, J. Virol. 60:157–166), these antibodies also recognized higher molecular weight forms on (FIG. 16B), corresponding in size to oligomers of gHt-gL.

Figure 17A:
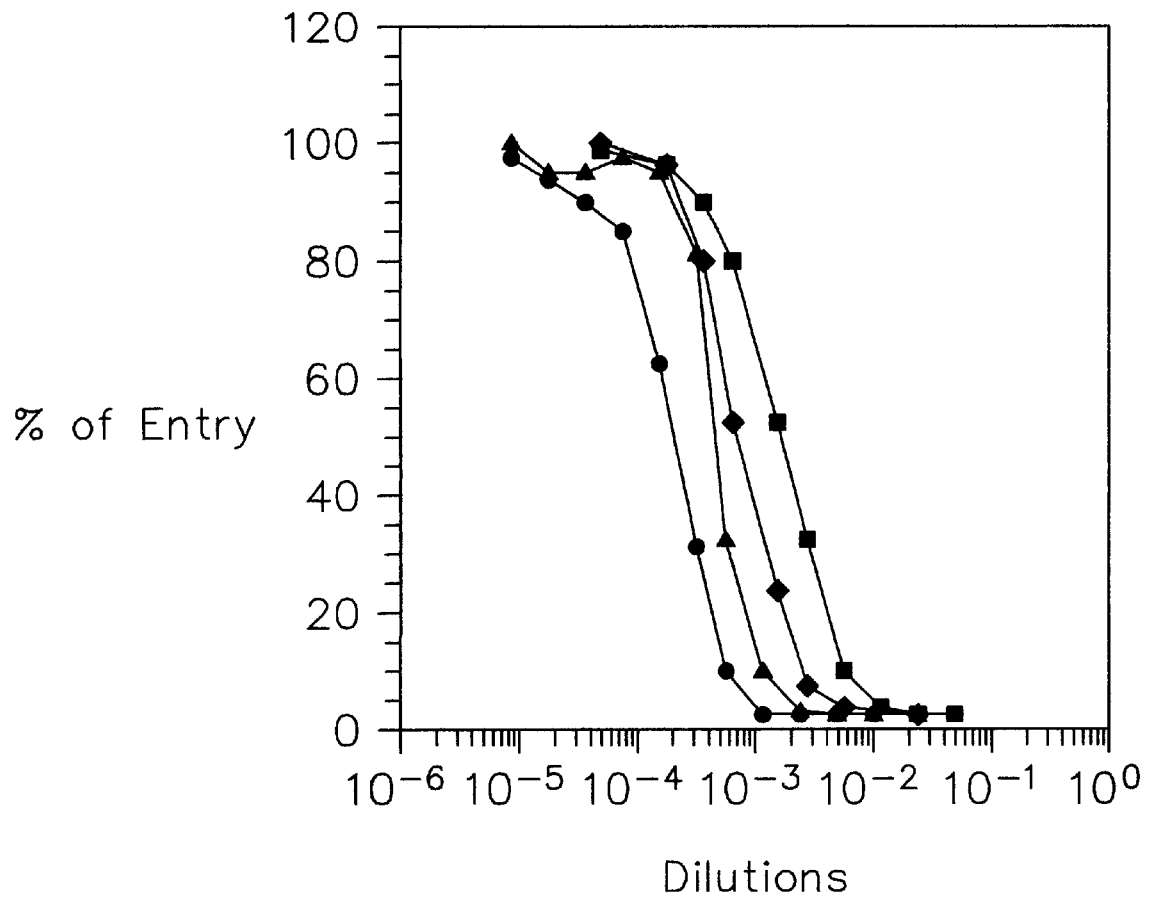
FIGS. 17A and 17B is a series of graphs depicting the effect of gHt-gL on HSV cell entry. Various concentrations of purified proteins gC1(457t) (gCt), gD-1(306t) (gDt) or gHt-gL were added to Vero cell monolayers in 96-well plates for 90 minutes at 4° C. HSV-1 strain hrR3 was added at an MOI of 0.5 and the plate was incubated for another 90 minutes at 4° C. Plates were then shifted to 37° C. for 5 hours. Cells were lysed and β-galactosidase activity was measured in aliquots of the cytoplasmic extract using the substrate CPRG and measuring the increase in absorption at 570 nm.

All four sera tested exhibited significant titers of complement independent HSV-1 neutralizing activity (Table 1). In addition these sera also neutralized HSV-2, albeit at a much reduced potency. These results indicated that the immunizing protein had biologic activity. In addition, each of the sera, when premixed with hrR3 virus, was able to block virus entry (FIG. 17A).

TABLE 1

HSV neutralizing activity of sera for rabbits immunized wlth gHt-gL

| | | Virus Neutralization Titer (50%) | | |
|---|---|---|---|---|
| Adjuvant | Rabbit | Entry assay[a] HSV-1 | Plaque assay[b] HSV-1 | Plaque assay[b] HSV-2(333) |
| Freund's | R136 (prebleed) | <1:20 | <1:20 | <1:20 |
| | R137 (prebleed) | <1:20 | <1:20 | <1:20 |
| | R136 (3rd bleed) | 1:640 | 1:640 | <1:20 |

TABLE 1-continued

HSV neutralizing activity of sera for rabbits immunized wlth gHt-gL

| | | Virus Neutralization Titer (50%) | | |
|---|---|---|---|---|
| Adjuvant | Rabbit | Entry assay[a] HSV-1 | Plaque assay[b] HSV-1 | Plaque assay[b] HSV-2(333) |
| | R137 (3rd bleed) | 1:4500 | 1:2000 | 1.60 |
| Alum | R138 (prebleed) | <1:20 | <1:20 | <1:20 |
| | R139 (prebleed) | <1:20 | <1:20 | <1:20 |
| | R138 (3rd bleed) | 1:2560 | 1:1800 | 1:100 |
| | R139 (3rd bleed) | 1:1280 | 1:640 | 1:100 |

[a]Virus entry was measured by infecting cells with HSV-1 strain hrR3 (Goldstein et al., 1998, supra) and measuring-galactosidase activity at 5 hours post infection. The neutralization titer represents the dilution of antiserum needed to reduce β-balactosidase activity to 50% of the maximum seen with no serum added.
[b]Virus infection was measured by plaque formation by HSV-1 strain KOS on Vero cells using the black plaque assay. The neutralization titer represents the dilution of antiserum needed to reduce the number of plaques to 50% of the number found on control plates with no anterium added.

Figure 17B:
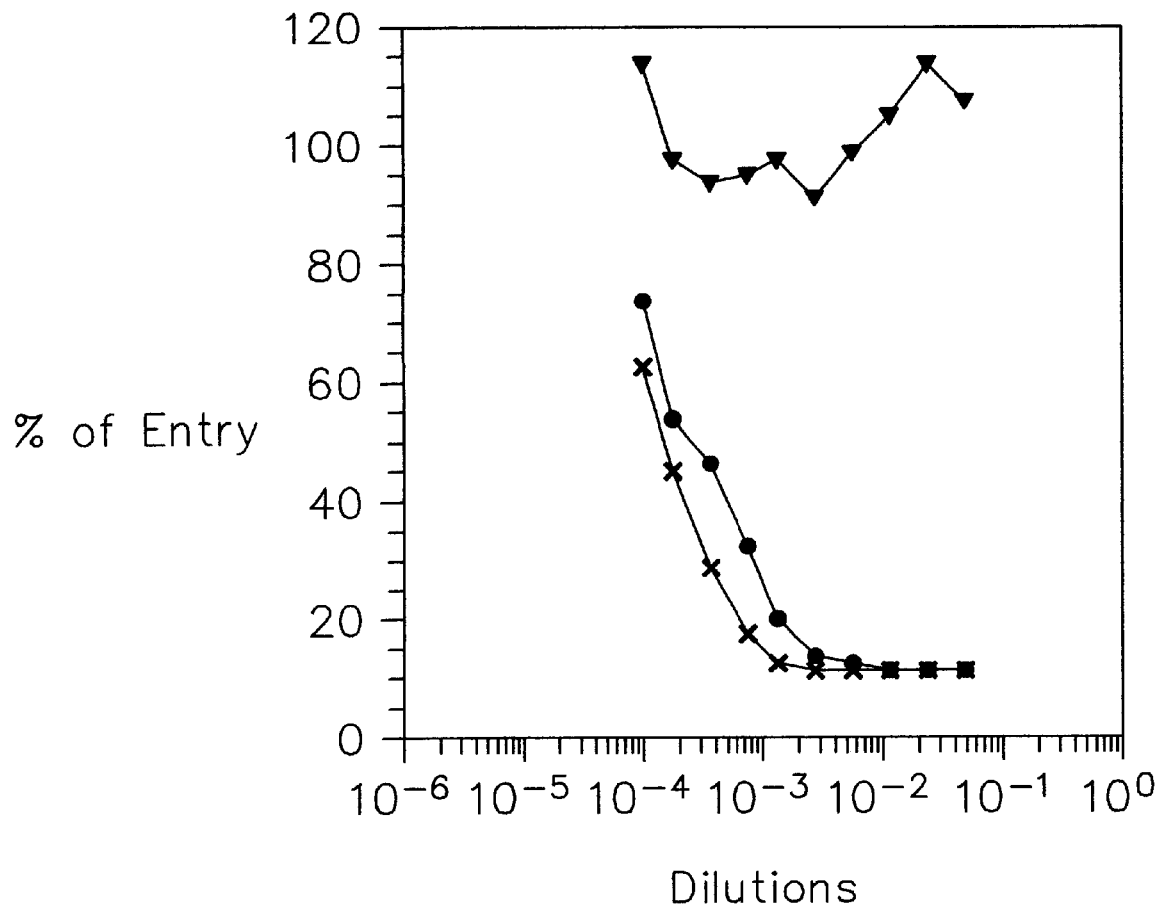

As a second approach, the virus was first adsorbed to cells at 4° C. and either R83 (anti-gH), R137, or MAb LP11 antibody was subsequently added to the virus-cell mixture. As expected, LP11 blocked virus entry when added after virus adsorption (FIG. 17B). R137 exhibited similar blocking activity to that observed for LP11, indicating that both antibodies recognized a site on gH-gL which was critical for post-binding steps in virus entry. This experiment suggests that the gHt-gL complex used to prepare R137 contains a functionally active conformation. In contrast, R83 antibody was unable to block virus entry. This was an important control for the present study because R83 had been prepared against gH purified from infected cells in such a way that it lacked gL and therefore lacked the proper biologically active conformation. (Roberts et al., 1991, Virology. 184:609–624). Thus, although it was not possible to directly demonstrate blocking activity by gHt-gL, the data provide indirect evidence that the complex contains the conformation necessary for function in virus infection.

Immunization of Mice with gHt-gL

To further assess the ability of gHt-gL to elicit a humoral immune response, Balb/c mice were immunized with gHt-gL in two separate experiments (Table 2). As positive controls, other mice were immunized with gD purified from HSV infected cells, and as negative controls, animals were sham-immunized with PBS. Prior to challenge with virus, serum samples were obtained from each of the immunized animals. The reactivity of a pool of mouse anti-gHt-gL serum (from Experiment I) was compared to that of R137 by immunoblotting. Both R137 and the mouse anti-gHt-gL reacted with gHt and gL on western blots (FIG. 17, lanes 1 and 5). R137 reacted with two bands of 66 kDa and 45 kDa in extracts from both infected and uninfected cells (FIG. 18, lanes 2, 3 and 4). Therefore, these bands are considered to be reacting non-specifically with the antibody. The reactivity of rabbit and mouse sera against cytoplasmic extracts of HSV-1 and HSV-2 infected cells was also compared. Both R137 and the pooled mouse serum reacted against bands migrating at the expected positions of gH-1 and gL-1 (FIG. 18, lanes 2 and 6). These sera also recognized the precursor forms of gH and gL. Both sera cross-reacted against bands presumed to be pgH-2 and gH-2 (FIG. 18, lanes 3 and 7). The mouse serum also reacted with a band at the presumed position of gL-2 (FIG. 18, lane 8). It should be noted that gL-2 is expected to be 500 Da larger than gL-1 based on predicted a amino acid sequence and gH-2 is predicted to be 700 Da smaller than gH-1.

TABLE 2

Protection of mice from intradermal HSV-1 challenge following immunization with gD or gHt-gL.

| Experiment[a] | Immunizing Antigen | Average 1° Score[b] (Sum of d3–d8) | Average 2° Score[c] (Sum of d3–d8) |
|---|---|---|---|
| I | Mock (PBS) | 10.5 | 16.5 |
|  | gD | 5.5 | 0 |
|  | gHt-gL | 2.8 | 0 |
| II | Mock (PBS) | 22.3 | 19.6 |
|  | gD | 5.8 | 0 |
|  | gHt-gL | 4.2 | 0 |

[a]In experiment I, there were ten mice in each group. One mouse in the gH-gL immunized group of experiment I died prior to challenge. Of the ten PBS infected animals, five died after virus challenge. Of the mice immunized with either gD or gH-gL, no mice died after virus challenge. In experiment II, there were five mice in each group. Of the five PBS infected animals, all died as a result of virus challenge. Of the five mice immunized with either gD or gH-gL, no mice died after virus challenge.
[b]Primary lesions developed immediately around the infection site. The primary scores were cumulative from day 3 to day 8. Score range was 0–5.
[c]Scored by the zosteriform lesions on the flank ssurrounding the primary infection site. The secondary scores with cumulative from days 3 to 8. Score range was 0–10.

Figure 19A:
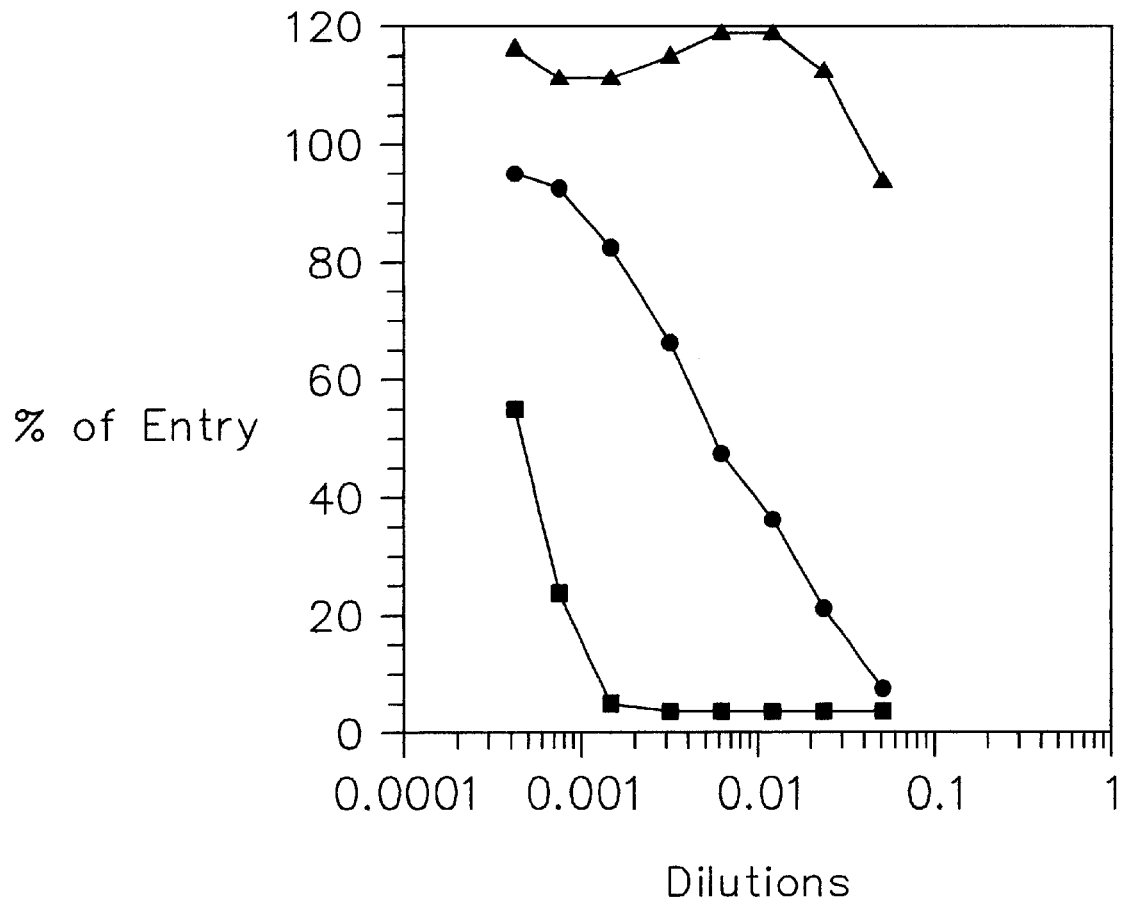
FIG. 19A: Filled squares correspond to gD, filled circles correspond to gHL, and filled triangles correspond to PBS. HSV-1 hrR3 was incubated for 90 minutes at 37° C. with various concentrations of antisera obtained from mice immunized either with full-length gD (obtained from HSV-1 infected cells) or with gHt-gL (obtained from HL-7 cells) or with PBS according to Experiment I (Table 2). The serum-virus mixture was added to Vero cell monolayers in a 96 well plate, incubated at 4° C. for 90 minutes and then at 37° C. for 5 hours. Virus entry was assayed as an increase in β-galactosidase activity in cytoplasmic extracts from each well and expressed as % of control values obtained with virus alone.
Figure 19B:
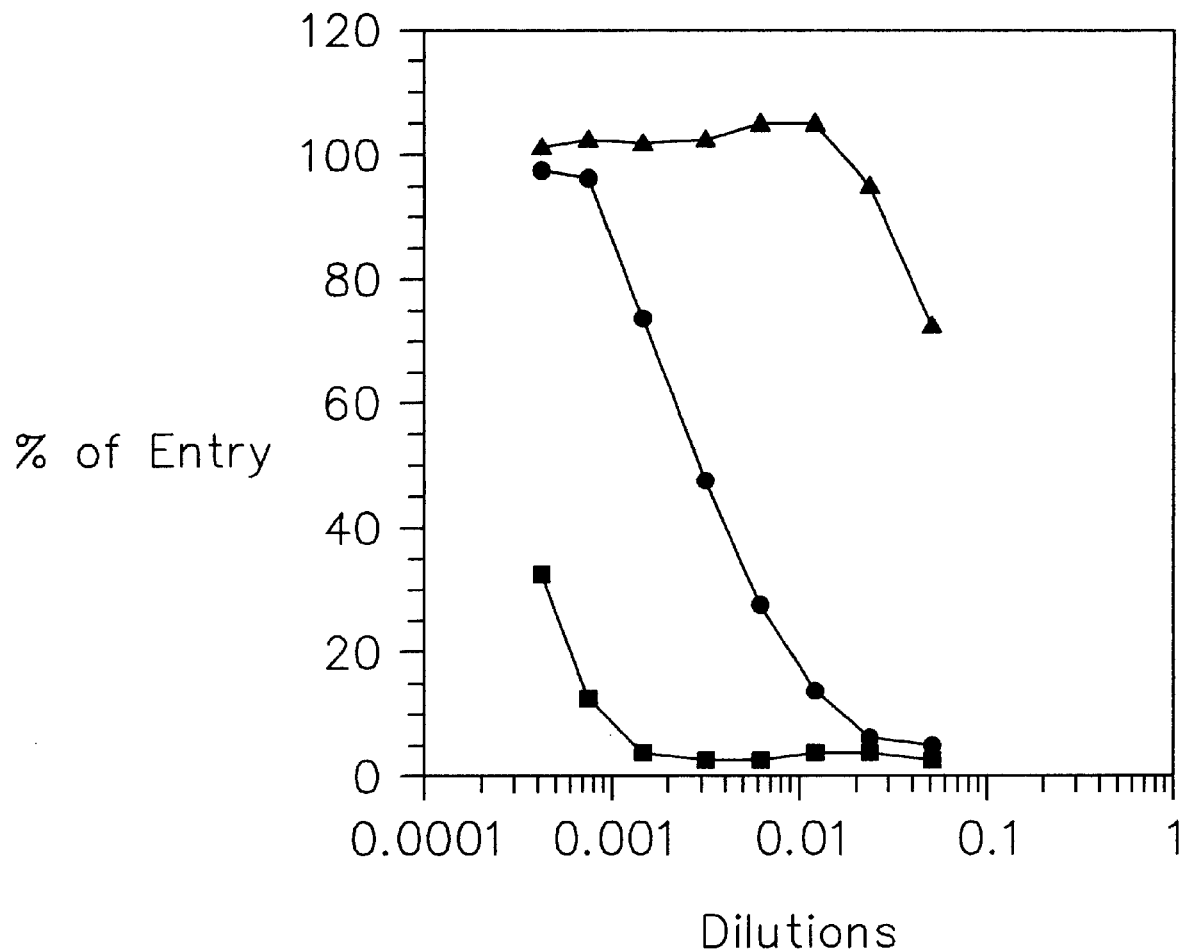
FIG. 19B: This is identical to FIG. 19A except that the sera were obtained from mice immunized as part of Experiment II (Table 2). Each of the sera from both experiments were assayed and only one representative curve for each experimental group is shown. All of the sera in each group yielded similar curves.

Sera obtained from each mouse immunized with either gD or gHt-gL exhibited high titers of virus neutralizing activity as measured by inhibition of virus entry (data for representative mice are shown in FIG. 19). It was observed that the titers were approximately tenfold higher when animals were immunized with gD as opposed to gHt-gL.

gHt-gL Protects Mice from HSV-1 Challenge

A zosteriform model of HSV-1 infection was used to examine the ability of gHt-gL to act as a vaccine (Simmons et al., 1985, J. Virol. 53:944–948; Simmons et al., 1984, J. Virol. 52:816–821). Following intraperitoneal immunization with either gD or gHt-gL, mice were challenged with HSV-1 by intradermal inoculation on the right flank (Table 2). In two separate experiments, some of the animals in each group exhibited some evidence of infection at the site of virus challenge (primary lesions). However, the primary lesion scores for mice immunized with either gD or gHt-gL were lower than those of sham-immunized mice. Of most significance was the finding that all of the sham-immunized mice that developed primary lesions went on to develop severe secondary zosteriform lesions. In contrast, mice which were immunized with either gD or with gHt-gL exhibited no secondary lesions, regardless of whether they developed any evidence of primary lesions. Furthermore, all of the immunized mice survived virus challenge, while many of the control animals died (5/10 in experiment I and 5/5 in experiment II). These results suggest that gHt-gL purified from HL-7 cells is biologically active and is a likely candidate for use as a subunit vaccine against HSV-1 infection.

Although neither gD nor gHt-gL were able to completely protect mice from developing lesions at the site of primary inoculation, both protein preparations ameliorated the severity of the primary disease. Significantly, prior immunization with either gD or gHt-gL gave excellent protection against development of zosteriform lesions. These data, together with the neutralization titers of anti-gHt-gL sera, are the most encouraging results seen to date regarding the potential efficacy of gHt-gL as a vaccine.

While this invention has been disclosed with reference to specific embodiments, it is apparent that other embodiments and variations of this invention may be devised by others skilled in the art without departing from the true spirit of the invention. The appended claims are intended to be construed to include all such embodiments and equivalent variations.

What is claimed is:

1. A vaccine comprising an isolated DNA encoding a soluble herpes simplex virus gHt-gL complex suspended in a pharmaceutically acceptable carrier.

2. The vaccine of claim 1, further comprising an isolated DNA encoding at least one of a herpes simplex virus gD, gB or gC.

3. A method of immunizing a human patient against a herpes simplex virus infection comprising administering to said patient the vaccine of claim 1.

4. A method of immunizing a human patient against a herpes simplex virus infection comprising administering to said patient the vaccine of claim 2.

5. A method of treating a herpes simplex virus infection in a human patient comprising administering to said patient the vaccine of claim 1.

6. A method of treating a herpes simplex virus infection in a human patient comprising administering to said patient the vaccine of claim 2.

7. A cell, the DNA of said cell encoding a soluble herpes simplex virus gHt-gL complex.

8. The cell of claim 7, wherein said cell is HL-7.

9. A method of modifying a cell to render it capable of secreting a soluble herpes simplex virus gHt-gL complex comprising introducing into said cell DNA encoding a truncated form of herpes simplex virus gH being gHt and full length herpes simplex virus gL, wherein said gHt and said gL are expressed in and secreted from said cell.

* * * * *